(12) United States Patent
Lynn

(10) Patent No.: US 7,398,115 B2
(45) Date of Patent: Jul. 8, 2008

(54) PULSE OXIMETRY RELATIONAL ALARM SYSTEM FOR EARLY RECOGNITION OF INSTABILITY AND CATASTROPHIC OCCURRENCES

(76) Inventor: Lawrence A. Lynn, 1502 Chambers Rd., Columbus, OH (US) 43212

( * ) Notice: Subject to any disclaimer, the term of this patent is extended or adjusted under 35 U.S.C. 154(b) by 79 days.

(21) Appl. No.: 11/148,325

(22) Filed: Jun. 9, 2005

(65) Prior Publication Data

US 2005/0240091 A1    Oct. 27, 2005

Related U.S. Application Data

(60) Continuation of application No. 10/162,466, filed on Jun. 3, 2002, now abandoned, which is a continuation-in-part of application No. 10/150,582, filed on May 17, 2002, now Pat. No. 7,081,095, said application No. 10/162,466 is a continuation-in-part of application No. 10/150,842, filed on May 17, 2002, which is a continuation-in-part of application No. 10/132,535, filed on Apr. 24, 2002, now Pat. No. 6,748,252, which is a division of application No. 09/776,771, filed on Feb. 6, 2001, now Pat. No. 6,760,608, which is a continuation of application No. 09/115,226, filed on Jul. 14, 1998, now Pat. No. 6,223,064, which is a continuation-in-part of application No. 08/789,460, filed on Jan. 27, 1997, now Pat. No. 5,891,023, which is a continuation of application No. 08/391,811, filed on Feb. 21, 1995, now Pat. No. 5,605,151, which is a continuation of application No. 08/151,901, filed on Nov. 15, 1993, now Pat. No. 5,398,682, which is a continuation-in-part of application No. 07/931,976, filed on Aug. 19, 1992, now abandoned.

(60) Provisional application No. 60/295,484, filed on Jun. 1, 2001, provisional application No. 60/291,687, filed on May 17, 2001, provisional application No. 60/291,691, filed on May 17, 2001, provisional application No. 60/052,438, filed on Jul. 14, 1997, provisional application No. 60/052,439, filed on Jul. 14, 1997.

(51) Int. Cl.
*A61B 5/00*    (2006.01)
*A61B 5/02*    (2006.01)
*A61B 5/08*    (2006.01)

(52) U.S. Cl. ............... 600/324; 600/483; 600/484; 600/529

(58) Field of Classification Search ............... 600/300, 600/310, 322, 323, 324, 336, 481, 483, 484, 600/529

See application file for complete search history.

(56) References Cited

U.S. PATENT DOCUMENTS

| | | |
|---|---|---|
| 4,106,503 A | 8/1978 | Rosenthal et al. |
| 4,365,636 A | 12/1982 | Barker |
| 4,523,279 A | 6/1985 | Sperinde |
| 4,630,614 A | 12/1986 | Atlas |
| 4,651,746 A | 3/1987 | Wall |
| 4,738,266 A | 4/1988 | Thatcher |
| 4,757,824 A | 7/1988 | Chaumet |
| 4,765,340 A | 8/1988 | Sakai |
| 4,802,485 A | 2/1989 | Bowers |
| 4,869,253 A | 9/1989 | Craig |
| 5,134,995 A | 8/1992 | Gruenke et al. |
| 5,199,424 A | 4/1993 | Sullivan |
| 5,206,807 A | 4/1993 | Hatke |
| 5,218,962 A | 6/1993 | Mannheimer et al. |
| 5,233,983 A | 8/1993 | Markowitz |
| 5,275,159 A | 1/1994 | Griebel |
| 5,303,699 A | 4/1994 | Bonassa et al. |
| 5,318,597 A | 6/1994 | Hauck et al. |
| 5,335,654 A | 8/1994 | Rapoport |
| 5,353,788 A | 10/1994 | Miles |
| 5,368,026 A | 11/1994 | Swedlow |
| 5,385,144 A | 1/1995 | Yamanishi |
| 5,398,682 A | 3/1995 | Lynn |
| 5,483,969 A | 1/1996 | Testerman et al. |
| 5,485,851 A | 1/1996 | Erickson |
| 5,490,502 A | 2/1996 | Rapoport et al. |
| 5,535,739 A | 7/1996 | Rapoport et al. |
| 5,540,733 A | 7/1996 | Testerman |
| 5,549,106 A | 8/1996 | Gruenke et al. |

| | | |
|---|---|---|
| 5,551,419 A | 9/1996 | Froehlich et al. |
| 5,605,151 A | 2/1997 | Lynn |
| 5,632,270 A | 5/1997 | O'Mahoney et al. |
| 5,645,053 A | 7/1997 | Remmers |
| 5,645,054 A | 7/1997 | Cotner |
| 5,682,878 A | 11/1997 | Ogden |
| 5,704,345 A | 1/1998 | Berthon-Jones |
| 5,730,144 A | 3/1998 | Katz et al. |
| 5,740,795 A | 4/1998 | Brydon |
| 5,743,250 A | 4/1998 | Gonda et al. |
| 5,749,900 A | 5/1998 | Schroeppel et al. |
| 5,751,911 A | 5/1998 | Goldman |
| 5,765,563 A | 6/1998 | Vander Schaaf |
| 5,769,084 A | 6/1998 | Katz |
| 5,782,240 A | 7/1998 | Raviv et al. |
| 5,794,614 A | 8/1998 | Gruenke et al. |
| 5,794,615 A | 8/1998 | Estes |
| 5,803,065 A | 9/1998 | Zdrojkowski et al. |
| 5,803,066 A | 9/1998 | Rapoport |
| 5,823,187 A | 10/1998 | Estes et al. |
| 5,827,179 A | 10/1998 | Lichter |
| 5,830,135 A | 11/1998 | Bosque |
| 5,845,636 A | 12/1998 | Gruenke et al. |
| 5,853,364 A | 12/1998 | Baker et al. |
| 5,865,173 A | 2/1999 | Froehlich |
| 5,865,736 A | 2/1999 | Baker |
| 5,891,022 A | 4/1999 | Pologe |
| 5,891,023 A | 4/1999 | Lynn |
| 5,902,250 A | 5/1999 | Verrier |
| 5,957,885 A | 9/1999 | Bollish |
| 6,006,379 A | 12/1999 | Hensley |
| 6,015,388 A | 1/2000 | Sackner |
| 6,083,156 A | 7/2000 | Lisiecki |
| 6,105,575 A | 8/2000 | Estes et al. |
| 6,120,441 A | 9/2000 | Griebel |
| 6,138,675 A | 10/2000 | Berthon-Jones |
| 6,144,877 A | 11/2000 | DePetrillo |
| 6,148,814 A | 11/2000 | Clemmer et al. |
| 6,216,032 B1 | 4/2001 | Griffin et al. |
| 6,223,064 B1 | 4/2001 | Lynn |
| 6,286,508 B1 | 9/2001 | Remmers et al. |
| 6,299,581 B1 | 10/2001 | Rapoport et al. |
| 6,305,374 B1 | 10/2001 | Zdrojkowski et al. |
| 6,342,039 B1 | 1/2002 | Lynn |
| 6,345,619 B1 | 2/2002 | Finn |
| 6,360,114 B1 * | 3/2002 | Diab et al. .................. 600/336 |
| 6,367,474 B1 | 4/2002 | Berthon-Jones et al. |
| 6,371,113 B1 | 4/2002 | Tobia et al. |
| 6,375,623 B1 | 4/2002 | Gavriely |
| 6,397,092 B1 | 5/2002 | Norris et al. |
| 6,401,713 B1 | 6/2002 | Hill et al. |
| 6,425,861 B1 | 7/2002 | Haberland et al. |
| 6,449,501 B1 * | 9/2002 | Reuss .......................... 600/323 |
| 6,463,326 B1 | 10/2002 | Hartley et al. |
| 6,488,634 B1 | 12/2002 | Rapoport et al. |
| 6,502,572 B1 | 1/2003 | Berthon-Jones et al. |
| 6,519,486 B1 | 2/2003 | Edgar |
| 6,529,752 B2 | 3/2003 | Krausman et al. |
| 6,532,960 B1 | 3/2003 | Yurko |
| 6,539,940 B2 | 4/2003 | Zdrojkowski et al. |
| 6,542,764 B1 * | 4/2003 | Al-Ali et al. ................ 600/323 |
| 6,609,016 B1 | 8/2003 | Lynn |
| 6,609,517 B1 | 8/2003 | Estes et al. |
| 6,622,726 B1 | 9/2003 | Du |
| 6,637,434 B2 | 10/2003 | Noble |
| 6,640,806 B2 | 11/2003 | Yurko |
| 6,661,161 B1 | 12/2003 | Lanzo et al. |
| 6,675,797 B1 | 1/2004 | Berthon-Jones |
| 6,684,090 B2 * | 1/2004 | Ali et al. ..................... 600/323 |
| 6,691,705 B2 | 2/2004 | Dittmann et al. |
| 6,745,764 B2 | 6/2004 | Hickle |
| 6,748,252 B2 | 6/2004 | Lynn |
| 6,760,608 B2 | 7/2004 | Lynn |
| 6,761,167 B1 | 7/2004 | Nadjafizadeh et al. |
| 6,804,656 B1 | 10/2004 | Rosenfeld et al. |
| 6,807,965 B1 | 10/2004 | Hickle |
| 6,814,074 B1 | 11/2004 | Nadjafizadeh et al. |
| 6,817,361 B2 | 11/2004 | Berthon-Jones et al. |
| 6,822,564 B2 * | 11/2004 | Al-Ali ........................ 600/322 |
| 6,832,200 B2 | 12/2004 | Greeven et al. |
| 6,896,660 B2 | 5/2005 | Jelliffe et al. |
| 6,932,084 B2 | 8/2005 | Estes et al. |
| 6,948,497 B2 | 9/2005 | Zdrojkowski et al. |
| 6,988,498 B2 | 1/2006 | Berthon-Jones |
| 7,123,950 B2 * | 10/2006 | Mannheimer ............... 600/323 |
| 2002/0117173 A1 | 8/2002 | Lynn et al. |
| 2002/0190863 A1 | 12/2002 | Lynn |
| 2003/0000522 A1 | 1/2003 | Lynn et al. |
| 2003/0127097 A1 | 7/2003 | Yurko |
| 2003/0137423 A1 | 7/2003 | Al-Ali |
| 2003/0158466 A1 | 8/2003 | Lynn |
| 2004/0073098 A1 | 4/2004 | Geva et al. |
| 2004/0170154 A1 | 9/2004 | Carter et al. |
| 2004/0230105 A1 | 11/2004 | Geva et al. |
| 2005/0016536 A1 | 1/2005 | Rapoport et al. |
| 2005/0027207 A1 | 2/2005 | Westbrook et al. |
| 2005/0081854 A1 | 4/2005 | Nadjafizadeh et al. |
| 2005/0240091 A1 | 10/2005 | Lynn |

FOREIGN PATENT DOCUMENTS

| | | |
|---|---|---|
| DE | 9 200 422.9 | 7/1992 |
| EP | 0459284 B1 | 1/1995 |
| EP | 0651971 A1 | 10/1995 |
| EP | 0709107 A1 | 5/1996 |
| EP | 0714670 A2 | 6/1996 |
| EP | 0722747 A2 | 7/1996 |
| EP | 0788805 A3 | 5/1998 |
| EP | 0968734 A3 | 1/2000 |
| EP | 1004325 A3 | 6/2000 |
| EP | 0700690 B1 | 2/2002 |
| EP | 0759791 B1 | 8/2002 |
| EP | 0934723 B1 | 9/2004 |
| EP | 1172123 B1 | 10/2004 |
| EP | 0875258 B1 | 11/2004 |
| EP | 1488743 A2 | 12/2004 |
| WO | WO 88/01149 | 2/1988 |
| WO | WO 90/09146 | 8/1990 |
| WO | WO 90/14121 | 11/1990 |
| WO | WO 92/11054 | 7/1992 |
| WO | WO 92/22244 | 12/1992 |
| WO | WO 94/06499 | 3/1994 |
| WO | WO 94/23780 | 10/1994 |
| WO | WO 95/32016 | 11/1995 |
| WO | WO 97/14462 | 4/1997 |
| WO | WO 97/28838 | 8/1997 |
| WO | WO 99/24099 | 5/1999 |
| WO | WO 99/45989 | 9/1999 |
| WO | WO 00/67827 | 11/2000 |
| WO | WO 2004/047621 A2 | 6/2004 |
| WO | WO 2005/065757 A1 | 7/2005 |

OTHER PUBLICATIONS

Blackshear et al., "Nocturnal dyspnea and artrial fibrillation predict Cheyne-Stokes respirations in patients with congestive heart failure," Arch Intern Med, vol. 155, Jun. 26, 1995, pp. 1297-1302.

Eppstein et al., "Cost-effectiveness analysis of nocturnal oximetry as a method of screening for sleep apnea-hypopnea syndrorome," Jan. 1, 1998, Chest, vol. 113, pp. 97-103.

Series et al., "Utility of Nocturnal Home Oximetry for Case Finding in Patients with Suspected Sleep Apnea Hypopnea Syndrome," Annl Int Med, 1993; 119-449 53.

Fletcher, et al., Rate of Oxyhemolgobin Desaturation in Obstructive versus Nonobstructive Apnea; Am Rev Respir Dis. 143:657-660, 1991.

Fletcher, et al., effect of Cardiac Output Reduction on rate of Desaturation in Obstructive Apnea; Chest, 99:452-456, 1991.

"Evaluation of Obstructive sleep Apnea in Singapore Using Computerized Polygraphic Monitoring" Tan and T.H. Koh, *Annals Academy of Medicine*, Mar. 1991, vol. 20 No. 2 pp. 196-200.

"Unattended CPAP Titration: Toward a smart Machine" G. Guilleminault, R. Stopha, L. Milea, J. Catiman, E. Kaitkawski.

Strohl et al. Oxygen Saturation During Breath Holding and During Apneas in Sleep, Chest, Feb. 1984: 85, No. 1: 181-186.

George et al. Identification on Qualification of Apneas by Computer-based Analysis of Oxygen Saturation, American Review of Respiratory Disease, 1988; 137: 1238-1240.

Slutsky et al. Quantification of Oxygen Saturation During Epiosodic Hypoxemia. American Review of Respiratory Disease, 1980; 121:893-895.

Gyulay et al. A Comparision of Clinical Assessment and Home Oximetry in the Diagnosis of Obstructive Sleep Apena. American Review of Respiratory Disease, 1993; 147: 50-53.

Pepin et al. Does Oximetry contribute to the Detection of Apneic Events? Mathematical, Processing of the $SaO_2$ Signal. Chest, May 1991; 99: 1151-1157.

Timmas et al. oxygen Saturation by Oximetry: analysis By Microcomputer, Journal of Polysomographic Technology; Spring 1988: 13-21.

Rauscher et al. Computerized Detection of Respirtory Events During Sleep from Rapid Increases in Oxyhemoglobin Saturation. Lung, 1991; 169: 355-42.

Rauscher et al. Quantification of sleep-disordered breathing by computerized analysis of oximetry, heart rate, and snoring. Eur Respir J. Jun. 1991; 4: 655-659.

Hoffarth, et al. "Beurteilung Pulsoximetrisch erfasster zklisheer . . ." and translation (Hoffarth et al. Assessment of Cyclic and Phasic Oxygen Desaturations Measured via Pulsoxymetry in Nocturnal Diagnosis of Respiratory Regulation Disorders, Peumologie, May 1991; 45: 229-232).

Aubry et al. A microcomputer system for monitoring and analyzing oxyhemoglobin saturation during sleep. Computer Programs in Biomedicine. 1984; 18: 227-234.

Fletcher, et al. The Rate of Fall of Arterial Oxyhemoglobin Saturation in Obstructive Sleep Apnea Chest. 1989; 96: 717-722.

Griffiths, et al. A video system for investigating breathing disorders during sleep. Thorad, 1991: 46: 136-140.

Hoch, et al. Oberprufung der Fruherkennungsmethode MESAM und biox 3700 zur erfassung schiafbezogener Atmungsregulationsstorungen bei jungen Mannem. Pheumologie, 1991; 45. 217-222 and translation.

Selmi, et al. Evaluation of Automatic Analysis of SC58. Airflow and Oxygen saturation signals in Patients with Sleep related Apneas. Chest, 1989; 96: 255-61.

Sanders, et al. Obstructive sleep Apnea Trated by Independently Adjusted Inspiratory and Expiratory Positive Airway Pressures via Nasal Mask. Chest, 1990: 98: 317-24.

Svanborg, et al A Limited Diagnostic Investigation for Static Charge Sensitive Bed. Chest, 1990: 98: 1341-45.

Kirby, et al. Computer quantitation of saturation impairment time as an index of oxygenation during sleep Com Meth, 1992; 107-115.

Series, et al., Influence of Continuous Positive Airways Pressure on Sleep apnea-related Desaturation in Sleep Apnea Patients. Lung, 1992; 170: 281-290.

Aubry, et al. The $SaO_2/t$ Diagram as a Useful Means To Express Nocturnal Hypoxemia. Chest, 1989; 96: 1341-45.

Evans, et al. A microcomputer system for monitoring and analysing oxyhemolobin saturation during sleep. Computer Programs in Biomedicine, 1984; 18: 227-234.

Longobardo et al., Sleep Apnea Considered As a Control System Instability, Sep. 1982, Respiratory Physiology 50: 311-333.

M.H. Wilkinson, et al Effect of venous ozygenation on arterial desaturation rate during repetitive apneas in lambs. Respiration Physiology 101 (1995) 321-331.

Steven M. Scharf, et al., Cardiovascular Effects of Periodic Occlusions of the Upper Airways in Dogs, American Review of Respiratory Disease, pp. 321-329.

U. Koehler, et al., Nocturnal Myocardial Ischemia and Cardiac Arrhythmia in Patients with sleep Apnea with an without Coronary Heart Disease (1991) 69; 474-482.

Guilleminault et al., "Sleep Apnea Syndrome: Can It Induce Hemodynamic Change?", Western Journal of Medicine, vol. 123, Jul. 1975, pp. 7-16.

Kehl, C. et al., Spektralanalyse von arterieller Sauerstoffsättigung und RR-Intervallen bei Patienten mit obstruktiver Schlafapnoe, Wein Med Wschr 1995, pp. 515-516 (vol. 145).

Shepard, J., Gas Exchange and Hemodynamics During Sleep, Medical Clinics of North America—vol. 69, No. 6, Nov. 1985, pp. 1243-1265.

Williams, et al. "Screening for Sleep Apnea Using Pulse Oximetry and A Clinical Score," CHEST, 100/3, Sep. pp. 631-635.

Rapoport, et al. "$CO_2$ homeostasis during periodic breathing: predictions from a computer model, "The American J of Applied Physiological, 1993, vol. 75, Issue 5, pp. 2302-2309.

Lynn, Lawrence A. "Cluster Analysis: A New Technology for the Evaluation of Oximetry and Airflow Waveforms in Obstructive Sleep Apnea," Accepted after revision on Dec. 20, 1997, 17 total pages.

Timms, et al. and Profox Associates, Inc., "Profox for the Bedside," Version 8SP 11/92, Programs for Oximetry [IBM], User's Manual, Nov. 1992, 20 total pages.

Standiforth et al., "Nocturnal desaturation in patients with stable heart failure", Heart, vol. 79, 1998, pp. 394-399.

Weiss, et al., "Computer Assisted Physiologic Monitoring and Stability Assessment in Vascular Surgical Patients Undergoing General Anesthesia—Preliminary Data," Journal of Clinical Monitoring and Computing, 16:107-113, 2000.

Patricia Buckle, et al., "Polysomnography In Acutely Ill Intensive Care Unit Patients," *Chest*, Jul. 1992, v. 102 n. 1 p. 288(4), American College of Chest Physicians.

Abraham, Howard et al., Sequential Cardiorespiratory Patterns in Septic Shock, Critical Care Medicine, vol. 11, No. 10, Oct. 1983, pp. 799-803.

Agilent Technologies, Agilent M1165/66/67/75/76/77A Component Monitoring System and Agilent M1205A V24 & V26, User's Reference Manual, vol. 1, System Information, Part Number M1046-9101L, First Ed., Printed Nov. 2000.

Agilent Technologies, Agilent M1165/66/67/75/76/77A Component Monitoring System and Agilent M1205A V24 & V26, User's Reference Manual, vol. 2, Parameter Information, Part Number M1046-9101L, First Ed., Printed Nov. 2000.

Alaris System, Brochure, Medication Safety System Focused at the Point of Care, Cardinal Health, Alaris Products, p. 8.

Bartolo, Anton, et al., An Arrhythmia Detector and Heart Rate Estimator For Overnight Polysomnography Studies, conditionally accepted for IEEE Transactions, 19 pages.

Benumof, Jonathan L., Creation of Observational Unit May Decrease Sleep Apnea Risk, Letters to the Editor, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.

Daley, Denise M., MD, Beware of All Sedatives in Patients With Sleep Apnea, Anesthesia Patient Safety Foundation Newsletter and posted on the Malpractice company's web site. The Doctors Company Sleep Apnea and Narcotic Postoperative Pain . . . http://www.thedoctors.com/risk/bulletins/sleepapnea.asp.

Dowdell, WT; Javaheri, S; McGinnis, W, Cheyne-Stokes Respiration Presenting as Sleep Apnea Syndrome. Clinical and Polysomnographic Features, Am Rev Respir Dis, Apr. 1990, pp. 871-879.

Dyken, Mark Eric et al., Obstructive Sleep Apnea Associated with Cerebral Hypoxemia and Death, Neurology 2004; 62, pp. 491-493.

Fisher, Kyle S., MD, Value of Pulse Oximetry Monitoring On the Ward is Questioned, Anesthesia Patient Safety Foundation Newsletter and posted on the Malpractice company's web site. The Doctors Company | Sleep Apnea and Narcotic Postoperative Pain . . . http://www.thedoctors.com/risk/bulletins/sleepapnea.asp.

Forster, Robert E., The Lung: Physiologic basis of Pulmonary Function Tests (Book), 1986 Year Book medical Publishers, Inc., Chapter 3, 1. Volume of Pulmonary Ventilation, pp. 32-64.

Gagnadoux, Frederick et al., Home Unattended vs Hospital Telemonitored Polysomnography in Suspected Obstructive Sleep Apnea Syndrome: A Randomized Crossover Trial, Chest 2002; 121; 753-758.

Gami, Apoor S. et al., Day-Night Pattern of Sudden Death in Obstructive Sleep Apnea, The New England Journal of Medicine, 2005; 352, pp. 1206-1214.

Jain, Sanjay S., et al., Perioperative Treatment of Patients with Obstructive Sleep Apnea, Current Opinion Pulmonary Medicine 10, pp. 482-488.

Pae, Eung-Kwon, et al., Neuroscience Letters 375, 2005, pp. 123-128.

Patil, Ramesh S. et al., Application of An Artificial Intelligence Program to Therapy of High Risk Surgical Patients, New Horizons, vol. 4, No. 4, pp. 541-550.

Ryan, Clodagh M., et al., Periodicity of Obstructive Sleep Apnea in Patients With and Without Heart Failure, Chest 2005; 127, pp. 536-542.

Shoemaker, W. C. et al., Incidence, Physiologic Description, Compensatory Mechanisms, and Therapeutic Implications of Monitored Events, Critical Care Medicine, Dec. 1989, vol. 17, No. 12, pp. 1277-1285.

Shoemaker, W. C. et al., Multicenter study of noninvasive monitoring systems as alternatives to invasive monitoring of acutely ill emergency patients, Chest, 1998; vol. 114; pp. 1643-1652.

Shoemaker, W. C. et al., Noninvasive Physiologic Monitoring of High-Risk Surgical Patients, Archives of Surgery, vol. 131, No. 7, Jul. 1996, pp. 732-737.

Shoemaker, W. C. et al., Prediction of Outcome and Severity of Illness by Analysis of the Frequency Distributions of Cardiorespiratory Variables, Critical Care Medicine, vol. 5, No. 2, Mar.-Apr. 1977, pp. 82-88.

Shoemaker, W. C. et al., Sequence of Physiologic Patterns in Surgical Septic Shock, Critical Care Medicine, Dec. 21, 1993 (12): pp. 1821.

Shoemaker, W. C., Cardiorespiratory Patterns in Complicated and Uncomplicated Septic Shock: Physiologic Alterations and Their Therapeutic Implications, Ann. Surg., Jul. 1971, vol. 174, No. 1, pp. 119-125.

Shoemaker, W. C., Early Physiologic Patterns in Acurate Illness and Accidents: Toward a Concept of Circulatory Dysfunction and Shock Based on Invasive and Noninvasive Hemodynamic Monitoring, New Horizons, Nov. 1996, vol. 4, No. 4, pp. 395-412.

Shoemaker, W.C., Oxygen Transport and Oxygen Metabolism in Shock and Critical Illness, Invasive and Noninvasive Monitoring of Circulatory Dysfunction and Shock, Critical Care Clinics, vol. 12, No. 4, Oct. 1996, pp. 939-969.

Shoemaker, W. C., Temporal Physiologic Patterns of Shock and Circulatory Dysfunction Based on Early Descriptions by Invasive and Noninvasive Monitoring, New Horizons, vol. 4, No. 2, May 1996, pp. 300-318.

Tatevossian, Raymond G., et al., Noninvasive Hemodynamic Monitoring for Early Warning of Adult Respiratory Distress Syndrome in Trauma Patients, Journal of Critical Care, vol. 15, No. 4 Dec. 2000, pp. 151-159.

Tatevossian, Raymond G., et al., Transcutaneous oxygen and C02 as early warning of tissue hypoxia and hemodynamic shock in critically ill emergency patients.

White, D. P., et al., Assessment of Accuracy and Analysis Time of a Novel Device to Monitor Sleep and Breathing in the Home, Sleep, vol. 18, No. 2, Feb. 1995, pp. 115-126.

Wilkins, Robert L., et al., Egan's Fundamentals of Respiratory Care, Analysis and Monitoring of Gas Exchange, Book, Eight Edition, Chapter 16, Section III, Capnography/Capnometry During Mechanical Ventilation, pp. 383-389.

Aboyans, V., et al., Sleep Apnoea Syndrome and the Extent of Atherosclerotic Lesions in Middle-Aged Men with Myocardial Infarction, International Angiology, Mar. 1999, vol. 18, No. 1, pp. 7073.

Aittokallio, Tero, et al., Analysis of Inspiratory Flow Shapes in Patients with Partial Upper-Airway Obstruction During Sleep, Chest, vol. 119, No. 1, Jan. 2001, pp. 37-44, Northbrook, IL, USA.

Alchanatis, M., et al., Left ventricular function in patients with obstructive sleep apnoea syndrome before and after treatment with nasal continuous positive airway pressure, Respiration, 2000, vol. 67, No. 4, p. 367, abstract.

Andreas, Stefan, et al., Prevalence of Obstructive Sleep Apnoea in Patients with Coronary Artery Disease, Coronary Artery Disease, Jul. 1996, vol. 7, No. 7, pp. 541-545.

Author Unknown, 1998 New Survey Reports More Than 168 Million American Adults Fail Sleep IQ Test, 132 Million Suffer Sleep Problems, Feb. 1998, Life Magazine.

Author Unknown, Background of Oximetry Utilization for Sleep Apnea Diagnosis, Publication information unknown, undated.

Author Unknown, Chapter IV Oxygen Consumption During ADO, Introduction, pp. 40-46, Book Title Unknown, date unknown.

Author Unknown, Chapter X Effects of a 6-minute Period of ADO, Introduction, pp. 108-113, Book Title Unknown, date unknown.

Author Unknown, Excessive Daytime Sleepiness, News Bulletin, http://www.websciences.org/nsf/pressarchives/leadpressrelease_g.html, Jun. 3, 1997, Washington, DC, USA.

Author Unknown, Guidance Article, (No Author), Critical Alarms and Patient Safety, Health Devices, vol. 31, No. 11, Nov. 2002, pp. 397-417, 2002 ECRI.

Author Unknown, News Bulletin, Lack of sleep America's top health problem, doctors say, Health Story Page, CNN, http://cnn.com/HEALTH/9703/17/nfm/sleep.deprivation/index.html, Mar. 17, 1997.

Author Unknown, Sleep Apnea & Heart Problems, News Channel WTVC, Chattanooga, Tennessee, USA, Jun. 3, 1999, News Bulletin.

Author Unknown, The Physiologic Parameters Defining the Oximetry Waveform Patterns in Sleep Apnea, undated, Publication Unknown.

Author Unknown, The Ventilation Instability Detection Trial, Hospital Protocol, Early Discussion Draft, 4 pages, Facsimile dated Jul. 23, 2003, From SDC.

Ayas, Najib, et al., Unrecognized Severe Postoperative Hypercapnia: A case of Apneic Oxygenation, Case Report, Mayo Clinic Proceedings, 1998, vol. 73, pp. 51-54, Minneapolis, Minnesota, USA.

Badoual, T., et al., Sleep Apnoea Syndrome and Cardiac Failure, Arch Mal Coeur Vaiss.; Mar. 2005, vol. 98, No. 3, pp. 198-202, [Article in French], abstract.

Bahammam, A., Comparison of nasal prong pressure and thermistor measurements for detecting respiratory events during sleep, Respiration, Jul.-Aug. 2004, vol. 71, No. 4, pp. 385-390, abstract.

Baker, Clark R., et al., Nellcor 04 Algorithm Summary, Copyright 1999 Mallinckrodt Inc., pp. 1-8.

Ball, Eric M., et al., Diagnosis and Treatment of Sleep Apnea Within the Community, The Walla Walla Project, Arch Intern Med, vol. 157, Feb. 24, 1997, pp. 419-424.

Barach, Alvan L., et al., The Physiologic Action of Oxygen and Carbon Dioxide on the Coronary Circulation, as Shown By Blood Gas and Electrocardiographic Studies, The American Heart Journal, Received for publication Aug. 14, 1940, pp. 13-38.

Barker, Steven J., The Effects of Motion on the Performance of Pulse Oximeters in Volunteers (Revised Publication), Anesthesiology, Lippincott-Raven Publishers, American Society of Anesthesiologists, Inc.(Revised Publication) 1997, vol. 86, pp. 101-108, both paper and abstract.

Barnum, P. T., et al., Novel Pulse Oximetry Technology Capable of Reliable Bradycardia Monitoring in the Neonate, Respiratory Care, 1997, vol. 42, No. 11, pp. 1072, abstract.

Bassetti, Claudio L., Sleep and Stroke, Seminars in Neurology, vol. 25, No. 1, Nov. 1, 2005, pp. 19-32.

Berg, Sören, et al., Continuous Intrathoracic Pressure Monitoring with a New Esophageal Microchip Catheter in Sleep-Related Upper Airway Obstructions, The Journal of Otolaryngology, vol. 24, No. 3, 1993, pp. 160-164.

Bernet-Buettiker, Vera et al., Evaluation of New Combined Transcutaneous Measurement of PC02/Pulse Oximetry Oxygen Saturation Ear Sensor in Newborn Patients, Dec. 15, 2004, DOI:10.1542/peds.2004-0946, Pediatrics Official Journal of the American Academy of Pediatrics, published online, pp. e-64-e68, Elk Grove Village, IL 60007, USA.

Berry, Richard B., et al., Comparison of Respiratory Event Detection by a Polyvinylidene Fluoride Film Airflow Sensor and a Pneumotachograph in Sleep Apnea Patients, Chest, The Cardiopulmonary and Critcal Care Journal, Chest/128/3/Sep. 2005, pp. 1331-1338, Northbrook, IL, USA.

Berry, Richard B., Positive Nasal Airway Pressure Eliminates Snoring as Well as Obstructive Sleep Apnea, Chest, vol. 85, No. 1, Jan. 1984, pp. 15-20.

Berthon-Jones, M., et al., Time Course of Change in Ventilatory Response to $CO_2$ with Long-Term CPAP Therapy for Obstructive Sleep Apnea, American Review Respiratoy Disease, 1987, vol. 135, pp. 144-147.

Berthon-Jones, Michael, Feasibility of A Self-Setting CPAP Machine Sleep, vol. 16, pp. S120-S123, 1993.

Bixler, E. O., et al., Effects of age on sleep apnea in men: I. Prevalence and Severity, American Journal of Respiratory & Clinical Care Medicine, vol. 157, No. 1, pp. 144-148, Jan. 1998, abstract.

Blankfield, R. P., et al., Bilateral leg edema, obesity, pulmonary hypertension, and obstructive sleep apnea, Arch Intern Med., Aug. 14, 2000, vol. 28, 160(15), pp. 2357-2362, abstract.

Blankfield, R. P., et al., Bilateral leg edema, pulmonary hypertension, and obstructive sleep apnea: a cross-sectional study, Family Practice, Jun. 2002, vol. 51, No. 6, pp. 561-564, abstract.

Block, A. Jay, et al., Sleep Apnea, Hypopnea and Oxygen Desaturation in Normal Subjects, A Strong Male Predominance, The New England Journal of Medicine, vol. 300, Mar. 8, 1979, pp. 513-517.

Blumen, M., et al., Dilator muscles of the pharynx and their implication in the sleep apnea syndrome of obstructive type. Review of the literature., [Article in French], Ann Otolaryngol Chir Cervicofac, May 1998, p. 115, abstract.

Bock, A. V. et al., The Oxygen and Carbon Dioxide Dissociation Curves of Human Blood (This is study No. 37 of a series of studies on the physiology and pathology of blood form the Harvard Medical School and allied Hospitals, a part of the expense of which has been defrayed by the Proctor Fund for the study of chronic disease, Journal of Biologic Chemistry, vol. 29, 1924, pp. 353-377.

Bohnhorst, B., et al., Major Reduction in Alarm Frequency With a New Pulse Oximeter, Intensive Care Medicine, 1998, vol. 24, No. 3, pp. 277-278, abstract.

Bordier, P., et al., Death during polysomnography of a patient with cheynestokes respiration, respiratory acidosis, and chronic heart failure, Chest, Nov. 2004, vol. 126, No. 5, pp. 1698-700, abstract.

Botelho, R. V., et al., Adult Chiari malformation and sleep apnoea, Neurosurg Review, Jul. 2005, vol. 28, No. 3, pp. 169-176, abstract.

Botelho, Ricardo Vieira, et al., Adult Chiari Malformation and Sleep Apnoea, Published online May 21, 2005, Neurosurgeon Review, vol. 28, pp. 169-176, 2005.

Boushra, N. N., Anaesthetic management of patients with sleep apnoea syndrome, Canadian Journal Anaesth, Jun. 1996, vol. 45, No. 6, pp. 599-616, abstract.

Bowton, David L., et al., The Incidence and Effect on Outcome of Hypoxemia in Hospitalized Medical Patients, The American Journal of Medicine, vol. 97, Jul. 1994, pp. 38-46.

Bradley, Douglas T., et al., Daytime Hypercapnia in the Development of Nocturnal Hypoxemia in COPD, Chest, vol. 97, No. 2, Feb. 1990, pp. 308-312.

Brooks, L. J., et al., Adenoid size is related to severity but not the number of episodes of obstructive apnea in children, Journal of Pediatrics, vol. 132, No. 4, pp. 682-686, Apr. 1998, abstract.

Broughton, Roger J., et al., Practice Parameters for the Use of Stimulants in the Treatment of Narcolepsy, ASDA Standards of Practice, Sleep, vol. 17, No. 4, pp. 348-351, American Sleep Disorders Association and Sleep Research Society 1994.

Brown, D. L., et al., Screening for obstructive sleep apnea in stroke patients: a cost-effectiveness analysis, Stroke, Jun. 2005, pp. 1291-1293, Epub May 12, 2005, abstract.

Brown, Lee K., "Dephlogisticated air" revisited: oxygen treatment for central sleep apnea, 1997 American College of Chest Physician, Physician Information, No. 8, Rev. 01, Nov. 1997.

Burk, John R., et al., Auto-CPAP in the Treatment of Obstructive Sleep Apnea: A New Approach, Sleep Research 21, 1992, p. 182, abstract.

Cain, S. M., Breaking Point of Two Breath Holds Separated by a Single Inspiration, Journal of Appl. Physiol., vol. II(I), Jul. 1957, pp. 87-90.

Campos-Rodriguez, Francisco, et al., Mortality in Obstructive Sleep Apnea-Hypopnea Patients Treated With Positive airway Pressure, Chest, The Cardiopulmonary and Critical Care Journal, 2005, vol. 128, pp. 624-633, Northbrook, Illinois, USA, plus abstract.

Cannesson, Maxime et al., Relation between respiratory variations in pulse oximetry plethsmographic waveform amplitude and arterial pulse pressure in ventilated patients, Critical Care 2005, vol. 9, #5, pp. R562-R568, Available online http://ccforum.com/content/9/5/R562.

Chaoquat, Ari, et al., Association of Chronic Obstructive Pulmonary Disease and Sleep Apnea Syndrome, American Journal Respiratory Critical Care Medicine, 1995, vol. 151, pp. 82-86.

Cherniack and Longobardo, Periodic Breathing During Sleep, pp. 158-190, New Jersey Medical School, Dean's Office, ID 9739727104, May 26, 1999, 14:23, No. 010, (first page missing).

Cherniack, N. S., Introduction to Session on the Pathophysiology of Breathing Control and Breathing: Awake and Asleep, Modeling and Control of Ventilation, Plenum Press, New York, USA, 1995, pp. 87-88.

Cherniack, N. S., New mechanisms for the cardiovascular effects of sleep apnea, American Journal Medicine, Nov. 1, 2000, vol. 109, No. 7, pp. 592-594, abstract.

Cherniack, Neil S., Oxygen Sensing: applications in humans, Highlighted Topic: Oxygen Sensing in Health and Disease, Journal Appl. Physiol., vol. 96, pp. 352-358, 2004, The American Physiological Society, http://www.jap.org.

Christiansen, J., et al., Carbon Dioxide in Blood, pp. 266-271, Proceedings of the Physiological Society, This Journal, XLVII, p. ii, 1913, pp. 266-271.

Cilli, Aykut, et al., Nocturnal Oxygen Desaturation in Coronary Artery Disease, JPN Heart Journal, Jan. 1999, pp. 23-28.

CNS Poly G, Printout Examples, CNS, Inc., Chanhassen, Minnesota, USA, Undated, Test Date Feb. 10, 1992.

Conte, G., et al., Acute cardiovascular diseases and respiratory sleep disorders, Minerva Cardioangiol, Jun. 1999, vol. 47, No. 6, pp. 195-202, abstract.

Cooper, B. G., et al., Value of Nocturnal Oxygen Saturation As A Screening Test for Sleep Apnoea, Thorax, 1991, vol. 46, pp. 586-588.

Coppola, Michael P., et al., Management of Obstructive Sleep Apnea Syndrome in the Home, The Role of Portable Sleep Apnea Recording, Chest, vol. 104, No. 1, Jul. 1993, pp. 19-24, Northbrook, IL, USA.

Coy, Timothy V., Sleep Apnoea and Sympathetic Nervous System Activity: A Review, Journal Slep Res., 1996, No. 5, pp. 42-50, European Sleep Research Society.

Decker, Michael J., et al., Ambulatory Monitoring of Arterial Oxygen Saturation, Chest, vol. 95, No. 4, Apr. 1989, pp. 717-722, Northbrook, Illinois, USA.

Deegan, P. C., et al., Predictive Value of Clincial Features for the Obstructive Sleep Apnoea Syndrome, European Respiratory Journal, vol. 9, pp. 117-124, 1996.

DeLeeuw, P.W., On sleep and death: cardiovascular risk the obstructive sleep apnea syndrome, Neth Journal Medicine, May 1999, vol .54, No. 5, pp. 188-190, abstract.

Dement, William C., Chairman, National Commission on Sleep Disorders Research, Wake Up America: A National Sleep Alert, vol. 1, Executive Summary and Executive Report, Report of the National Commission on Sleep Disorders Research, Submitted to the United States Congress and to the Secretary, u.s. department of Health and Human Services, Jan. 1993, pp. 1-76.

Demeter, P., et al., The relationship between gastroesophageal reflux disease and obstructive sleep apnea, Gastroenterology, Sep. 2004, vol. 39, No. 9, pp. 815-820, abstract.

Dempsey, Jerome A., et al., Sleep and Breathing State of the Art Review Sleep-Induced Breathing Instability, Sleep, vol. 19, No. 3, pp. 236-247, American Sleep Disorders Association and Sleep Research Society.

Den Herder, Cindy et al., Risks of general anaesthesia in people with obstructive sleep apnea, BMJ, vol. 329, Oct. 23, 2004, pp. 955-959, Downloaded from bmj.com.

Dhonneur, G., et al., Postoperative Obstructive Apnea, Anesth Analg., Sep. 1999, vol. 89, No. 3, pp. 762-767, abstract.

Doherty, L. S, et al., Long-term effects of nasal continuous positive airway pressure therapy on cardiovascular outcomes in sleep apnea syndrome, Chest, Jun. 2005, vol. 127, No. 6, pp. 2076-2084, abstract.

Douglass, A. B., et al., The Sleep Disorders Questionnaire. I: Creation and multivariate structure of SDQ, Sleep, Mar. 1994, vol. 17, No. 2, pp. 160-167, abstract.

Douglass, Alan B., et al., The Sleep Disorders Questionnaire I: Creation and Multivariate Structure of SDQ, Clinical Research, Sleep, vol. 17, No. 1, pp. 160-167, 1994 American Sleep Disorders Association and Sleep Research Society.

Dumas, Constantine, et al., Clinical Evaluation of a Prototype Motion Artifact Resistant Pulse Oximeter in the Recovery Room, Anesth Analg 1996, vol. 83, pp. 269-272.

Dursunoglu, D., et al., Impact of obstructive sleep apnoea on left ventricular mass and global function, European Respiratory Journal, Aug. 2005, vol. 26, No. 2, pp. 283-288, abstract.

Dyken, M. E., et al., Obstructive sleep apnea associated with cerebral hypoxemia and death, Neurology, Feb 10, 2004, vol. 62, No. 3, pp. 491-493, abstract.

Dziewas, R., et al., Capnography screening for sleep apnea in patients with acute stroke, Neurology Res. Jan. 2005, vol. 27, No. 1, pp. 83-87, abstract.

Dziewas, R., et al., Increased Prevalence of Sleep Apnea in Patients with Recurring Ischemic stroke Compared with First Stroke Victims, Journal Neurology, Nov. 2005, vol. 252, No. 11, pp. 1394-1398. Epub Jul. 20, 2005, abstract.

Edge City Hospital Sleep Disorders Center, Sleep Summary of Patient, Houston, Texas, USA, pp. 1-3, Feb. 17, 1997.

Elfadel, I. M., et al., Motion-Resistant Pulse Oximetry, Abstract Only, Journal of Clinical Monitoring, vol. II, No. 4, Jul. 1995, p. 262.

Eihefnawy, Ahmed, et al., Stability Analysis of CO2 Control of Ventilation, Journal of Internal Medicine, 0161-7567/90, pp. 498-503, Publisher: The American Physiological Society, 1990.

Escourrou, P., et al., Heart failure and sleep respiratory disorders. Prevalence, physiopathology and treatment, [Article in French], Rev Mal Respir, Jun. 2000, vol. 17, Suppl 3, pp. S31-S40, abstract.

Farhi, Leon E., et al., Dynamics of Changes in Carbon Dioxide Stores, Anesthesiology, Nov.-Dec. 1960, vol. 21, pp. 604-614 (last page missing).

Farney, Robert J., et al., Ear Oximetry to Detect Apnea and Differentiate Rapid Eye Movement (REM) and Non-REM (NREM) Sleep, Screening for the Sleep Apnea Syndrome, Chest, vol. 89, No. 4, Apr. 1986, pp. 533-539, Northbrook, IL, USA.

Farre, R., et al., Importance of the Pulse Oximeter Averaging time When Measuring Oxygen Desaturation in Sleep Apnea, Sleep, Jun. 15, 1998, vol. 21, No. 4, pp. 386-390 Missing pages 386 and 390.

Feinsilver, Steven H., Current and Future Methodology for Monitoring Sleep, Sleep Disorders, Clinics in Chest Medicine, vol. 19, No. 1, Mar. 1998, Published from the Division of Pulmonary Medicine, North Shore University Hospital, Manhasset, New York, NY, USA.

Ferber, Richard, et al., Portable Recording in the Assessment of Obstructive Sleep Apnea, ASDA Standards of Practice, American Sleep Disorders Association, 1610 14th Street, NW, Suite 300, Rochester, MN 55901-2200, USA.

Findley, Larry J., et al., Cheyne-Stokes Breathing During Sleep in Patients With Left Ventricular Heart Failure, Southern Medical Journal, vol. 78, No. 1, Jan. 1985, pp. 11-15.

Findley, Larry J., et al., Sleep Apnea and Auto Crashes, What is the Doctor to do?, Chest, vol. 94, No. 2, Aug. 1988, pp. 225-226.

Fiz, J. A., et al., Acoustic Analysis of Snoring Sound in Patients with Simple Snoring and Obstructive Sleep Apnoea, European Respiratory Journal, 1996, vol. 9, pp. 2365-2370, Printed in the United Kingdom.

Flemons, W. Ward, et al., Sleep Apnea and Cardiac Arrhythmias, Is There A Relationship?, American Review Respiratory Disease, vol. 148, pp. 618-621, 1993.

Fletcher, Eugene C., et al., Nocturnal Oxyhemoglobin Desaturation in COPD Patients with Arterial Oxygen Tensions Above 60 mm Hg, Chest, vol. 92, No. 4, Oct. 1987, pp. 604-608.

Forster, R. E., et al., Time course of exchages between red cells and extracellular fluid during $CO_2$ uptake, Journal of Applied Physiology, vol. 38, No. 4, Apr. 2975, Printed in U.S.A.

Franklin, K. A., et al., Reversal of Central Sleep Apnea with Oxygen, Chest, Jan. 1997, vol. 111, No. 1, pp. 163-169, abstract.

Freid, E. B., The rapid sequence induction revisited: obesity and sleep apnea syndrome, Anesthesiol Clin North America, Sep. 2005, vol. 23, No. 3, pp. 551-564, abstract.

Frumin, Jack M., Apneic Oxygenation in Man, Anesthesiology, vol. 20, pp. 789-798, 1959.

Gami, A. et al., Day-night pattern of sudden death in obstructive sleep apnea, New England Journal Medicine, Mar. 24, 2005, vol. 352, No. 12, pp. 1206-1214, abstract.

Gangitano, E. S., et al., Near Continuous Pulse Oximetry During Newborn ECLS, ASAI Journal, 1999, vol. 45, No. 1, p. 125, abstract.

Gaultier, C., Upper airway muscles and physiopathology of obstructive sleep apnea syndrome, [Article in French], Neurophysiol Clin, Jun. 1994, vol. 24, No. 3, pp. 195-206, abstract.

Gavin, T. P., et al., The effect of exercise modality on exercise-induced hypoxemia, Respiration Physiology, May 3, 1999, vol. 115, No. 3, pp. 317-323, abstract.

Gentil, Benoit, et al., Enhancement of Postoperative Desaturation in Heavy Snorers, Anesth Analg 1995, vol. 81, pp. 389-392.

George, Charles Frederick Petersen, Diagnostic Techniques in Obstructive Sleep Apnea, Progress in Cardiovascular Diseases, vol. 41, No. 5, Mar./Apr. 1999, pp. 355-366.

Glerant, J. C., et al., Intensive care and respiratory sleep disorders, [Article in French], Rev Mal Respir, Dec. 1999, vol. 16, No. 6, pp. 1091-1104, abstract.

Gold, Avram R., et al., Impact of Basic Research on Tomorrow's Medicine, The Pharyngeal Critical Pressure, The Whys and Hows of Using Nasal Continuous Positive Airway Pressure Diagnostically, Chest, vol. 110, No. 4, Oct. 1996, pp. 1077-1088, Northbrook, IL USA.

Goldberger, Ary L., et al., Components of a New Research Resource for Complex Physiologic Signals, PhysioBank, PhysioToolkit, and PhysioNet, American Heart Association Journals, Circulation, vol. 101, No. 23, pp. 1-9, 2000, Circulation, 2000:101:e215, http://circ.ahajournals.org/cgi/content/ful/101/23/e215.

Goldstein, M. R., et al., Pulse Oximetry in Transport of Poorly-Perfused Babies, Abstract only, Pediatrics, 1998, vol. 102, No. 3, p. 818.

Goode, Richard L., Who needs a sleep test? The value of the history in the diagnosis of obstructive sleep apnea, http://www.findarticles.com/p/articles/mi_m0BUM/is_9_78/ai_56229331/print, Sep. 1999.

Goodfriend, Theodore L., et al., Resistant Hypertension, Obesity, Sleep Apnea, and Aldosterone: Theory and Therapy, Hypertension, Journal of the American Heart Association, published online Jan. 19, 2004, Print ISSN: 0194-911X. Online ISSN: 1524-4563, pp. 518-524, Dallas, Texas, USA.

Grap, Mary Jo, Protocols for Practice, Applying Research at the Bedside, Critical Care Nurse, vol. 18, No. 1, Feb. 1998, pp. 94-99.

Greco, J. M., et al., Long-term Airway Space Changes after Mandibular Setback Using Bilateral Sagittal Split Osteomy, Internal Journal Oral Maxillofac. Surg. 1990, vol. 19, pp. 103-105.

Greco, Joan M., Cephalometric Analysis of Long-Term Airway Space Changes with Maxillary Osteotomies, Oral Surg Oral Med Oral Pathol, Nov. 1990, vol. 70, No. 5, pp. 552-554.

Grimm, W., et al., Outcome of patients with sleep apnea-associated severe bradyarrhythmias after continuous positive airway pressure therapy, American Journal Cardiology, Sep. 15, 2000, vol. 86, No. 6, pp. 688-692, abstract.

Grote, Ludger, et al., Finger Plethysmography—A Method for Monitoring Finger Blood Flow During Sleep Disordered Breathing, Respiratory Physiology & Neurobiology, vol. 136, 2003, pp. 141-152, Publisher: Elsevier.

Grunstein, Ronald R., et al., Treatment of Sleep Disordered Breathing, Position Statement, The Medical Journal of Australia, vol. 154, Mar. 4, 1991, pp. 355-359, Australia.

Gugger, M., Comparison of ResMed AutoSet (version 3.03) with polysomnography in the diagnosis of the sleep apnea/hypopnoea syndrome, European Respiratory Journal, Mar. 1997, vol. 10, No. 3, pp. 587-591, abstract.

Guilleminault, C., et al., Maxillo-mandibular surgery for obstructive sleep apnoea, European Respiratory Journal, 1989, vol. 2, pp. 604-612.

Guilleminault, C., et al., Sleep-disordered breathing in children, Annals of Medicine, vol. 30, No. 4, pp. 350-356, Aug. 1998, abstract.

Guilleminault, Christian, et al., A Cause of Excessive Daytime Sleepiness, The Upper Airway Resistance Syndrome, Chest, vol. 104, No. 3, Sep. 1993, pp. 781-787.

Guilleminault, Christian, et al., The Sleep Apnea Syndromes, Copyright 1976, Citation Annual Review of Medicine, vol. 27: 465-484 (Volume publication date Feb. 1976).

Guilleminault, Christian, Obstructive Sleep Apnea, The Clinical Syndrome and Historical Perspective, Medical Clinics of North America, vol. 69, No. 6, Nov. 1985, pp. 1187-1203, Stanford, California, USA.

Gupta, R. M., et al., Perioperative cardiopulmonary evaluati and management: are we ignoring obstructive sleep apnea syndrome?, chest, Dec. 1999, vol. 116, No. 6, p. 1843, abstract.

Gupta, Rakesh M., et al., Postoperative Complications in Patients with Obstrucitve Sleep Apnea Syndrome Undergoing Hip or Knee Replacement: A Case-Control Study, Mayo Clinic Proceedings, 2001, vol. 76, pp. 897-905, Rochester, MN, USA.

Gyulay, Stephen, et al., Evaluation of A Microprocessor-Based Portable Home Monitoring System to Measure Breathing During Sleep, Sleep, vol. 10, No. 2, pp. 130-142, Raven Press, New York, USA, 1987, Association of Professional Sleep Societies.

Hanley, Patrick, et al., Pathogenesis of Cheyne-Stokes Respiration in Patients with Congestive Heart Failure, Relationship to Arterial $Pco_2$, Chest, vol. 104, No. 4, Oct. 1993, pp. 1079-1084.

Hanly, P. J., et al., Increased Mortality Associated with Cheyne-Stokes Respiration in Patients with Congestive Heart Failure, American Journal Respiratory Critical Care Medicine, Jan. 1996, vol. 153, No. 1, 272-6, abstract.

Hanly, Patrick J., et al., Respiration and Abnormal Sleep in Patients with Congestive Heart Failure, Chest, vol. 96, No. 3, Sep. 1989, pp. 480-488.

Hanly, Patrick, et al., ST-Segment Depression During Sleep in Obstructive Sleep Apnea, The American Journal of Cardiology, vol. 71, Jun. 1, 1993, pp. 1341-1345.

Harbison, J., et al., Cardiac rhythm distrubances in the obstructive sleep apnea syndrome: effects of nasal continuous positive airway pressure therapy, Chest, Sep. 2000, vol. 118, No. 3, pp. 591, abstract.

Hatta, K., et al., Prolonged upper airway instability in the parenteral use of benzodiazepine with levomepromazine, Journal Clin Psychopharmacol, Feb. 2000, vol. 20, No. 1, pp. 99, abstract.

He, Jiang, et al., Mortality and Apnea Index in Obstructive Sleep Apnea, Experience in 385 Male Patients, Clinical Investigations, Chest, vol. 94, No. 1, Jul. 1988, pp. 9-14.

Health Devices, Next-Generation Pulse Oximetry, Special Issue, Feb. 2003, vol. 32, No. 2, Plymouth Meeting, PA, USA.

Henderson, L. J., et al., Blood as a Physicochemical System. II, pp. 426-431, Paper.

Hillman, David R., et al., Obstructive Sleep Apnoea and Anaesthesia, Sleep Medicine Reviews, 2004, vol. 8, pp. 459-472, Publisher: Elsevier.

Hoffman, Eric A., et al., Multimodality Imaging of the Upper Airway: MRI, MR Spectroscopy, and Ultrafast X-ray CT, Sleep and respiration, 1990 Wiley-Liss, Inc., pp. 291-301.

Hoffmann, M., et al., Sleep apnea and hypertension, Minerva Med., Aug. 2004, vol. 95, No. 4, pp. 281-290, abstract.

Hoffstein, Victor, Blood Pressure, Snoring, Obesity, and Nocturnal Hypoxaemia, The Lancet, vol. 344, Sep. 3, 1994, pp. 643-645.

Hoffstein, Victor, et al., Cardiac Arrhythmias, Snoring, and Sleep Apnea, Chest, 1994, vol. 106, pp. 466-471, Northbrook, IL, USA.

Hoffstein, Victor, et al., Snoring and Arousals: A Retrospective Analysis, Sleep, vol. 18, No. 10, pp. 866-882, 1995 American Sleep Disorders Association and Sleep Research Society.

Holmes, Michael, et al., Co-Oximetry Validation of a New Pulse Oximeter in Sick Newborns, Respiratory Care, 1998, vol. 43, No. 10, pp. 860, abstract.

Hung, Joseph, et al., Association of Sleep Apnoea with Myocardial Interfarction in Men, The Lancet, vol. 336, pp. 261-264, Jul. 28, 1990, Abstract only, p. 261.

Isono, S., et al., Anatomy of pharynx in patients with obstructive sleep apnea and in normal subjects, Journal Appl Physiol, Apr. 1997, vol. 82, No. 4, pp. 1319-1326, abstract.

Isono, S., et al., Interaction of cross-sectional area, driving pressure, and airflow of passive velopharynx, Journal Appl Physiol, Sep. 1997, vol. 83, No. 3, pp. 851-859, abstract.

Isono, S., et al., Static mechanics of the velopharynx of patients with obstructive sleep apnea, Journal Appl Physiol, Jul. 1999, vol. 75, No. 1, pp. 148-154, abstract.

Jarrell, L., Preoperative diagnosis and postoperative management of adult patients with obstructive sleep apnea syndrome: a review of the literature, Journal Perianesth Nursing, Aug. 1999, vol. 14, No. 4, pp. 193-200, abstract.

Javaheri, S., Effects of continuous positive airway pressure on sleep apnea and ventricular irritability in patients with heart failure, Circulation, Feb. 1, 2000, vol. 101, No. 4, pp. 392-397, abstract.

Javaheri, S., et al., Occult Sleep-Disordered Breathing in Stable Congestive Heart Failure, Annuals Internal Medicine, Apr. 1995, vol. 122, No. 7, pp. 487-492, abstract.

Javaheri, S., et al., Sleep Apnea in 81 Ambulatory Male Patients With Stable Heart Failure, Types and Their Prevalences, Consequences, and Presentations, Received Nov. 20, 1997; revision received Jan. 23, 1998, accepted Jan. 28, 1998, From the Sleep Disorders Laboratory, Department of Veterans Affairs Medical Center, and the Department of Medicine, University of Cincinatti, College of Medicine, Cincinnati, Ohio.

Johnson, J. T., et al., Preoperative, Intraoperative, and postoperative management of patients with obstructive sleep apnea syndrome, Otolaryngol Clin North America, Dec. 1998, vol. 31, No. 6, pp. 1025-1030, abstract.

Jones, N. L., et al., The Estimation of Carbon Dioxide Pressure of Mixed Venous Blood During Exercise, Clinical Science (1967), vol. 32, pp. 311-327.

Juhász, János, et al., Unattended Continuous Positive Airway Pressure Titration, Clinical Relevance and Cardiorespiratory Hazards of the Method, American Journal Respiratory Critical Care Medical, vol. 154, pp. 359-365, 1996.

Kabeli, Cheryl, Obstructive Sleep apnea and Modifications in Sedation, Critical Care Nursing Clinics of North America, vol. 17, 2005, pp. 269-277, ccnursing.theclinics.com, Publisher: Elsevier Saunders.

Kalra, Maninder, et al., Obstructive Sleep Apnea in Extremely Overweight Adolescents Undergoing Bariatric Surgery, Obesity Research, vol. 13, No. 7, Jul. 2005, pp. 1175-1179.

Kanagala, Ravi, et al., Obstructive Sleep Apnea and the Recurrence of Atrial Fibrillation, Circulation, May 27, 2003, pp, 2589-2594, American Heart Association, Inc.

Kaplan, Joseph, Beginner's Atlas of Overnight Oximetry, Apr. 10, 1995, Mayo Clinic, Jacksonville, Florida, USA, Copyright 1986, PROFOX Associates, Inc.

Kaplan, Joseph, et al., Home Pulse Oximetry As A Screening Test for Sleep-Disordered Breathing, Chest, vol. 103, pp. 322S, Northbrook, IL, USA.

Kapur, V. K., et al., Association of hypothyroidism and obstructive sleep apnea, American Journal of Respiratory & Critical Care Medicine, vol. 158, No. 5 Pt. 1, pp. 1379-1383, Nov. 1998, abstract.

Kapur, V., et al., The medical cost of undiagnosed sleep apnea, Sleep, Sep. 1999, vol. 22, No. 6, pp. 749-755, abstract.

Katchen, Marc, et al., Evaluation of the Sleepy Crewmember: USAFSAM Experience and a Suggested Clinical Approach, Aviation, Space and Environmental Medicine, Mar. 1989, pp. 263-267.

Kaw, Roop, et al., Unrecognized Sleep Apnea in the Surgical Patient, Implications for the Perioperative Setting, Chest, 2006, vol. 129, pp. 198-205.

Kawai, Mitsuru, et al., Nocturnal hypoxia index: A new pulse oximetry index of nocturnal hypoventilation in neuromuscular disorders, Clinical Neurology, vol. 35, pp. 1003-1007, 1995, abstract.

Kimmel, Paul L., et al., Sleep Apnea syndrome In Chronic renal Disease, The American Journal of Medicine, vol. 86, Mar. 1989, pp. 308-314.

King, E. D., et al., A model of obstructive sleep apnea in normal humans. Role of the upper airway., American Journal Respiratory Critical Care Medicine, Jun. 2000, vol. 161, No. 6, pp. 1979-1984, abstract.

Kirby, S.D., et al., Neural network prediction of obstructive sleep apnea from clinical criteria, Chest, vol. 116, No. 2, pp. 409-415, Aug. 1999, abstract.

Kirby, Stan C., et al., Section II. Systems and programs, Computer quantitation of saturation impairment time as an index of oxygenation during sleep, Computer Methods and Programs in Biomedicine, vol. 38, 1992, pp. 107-115, Elsevier Science Publishers B.V.

Klocke, F. J., et al., Breath holding after breathing of oxygen, Journal Appl. Physiol., vol. 14, No. 5, pp. 689-693, 1959.

Koehler, U., et al., Heart Block in Patients with Obstructive Sleep Apnoea: Pathogenetic Factors and Effects of Treatment, European Respiratory Journal, 1998, vol. 11, pp. 434-439, Printed in United Kingdom.

Kolobow, Theodor, et al., Intratracheal Pulmonary Ventilation (ITPV); Control of Positive End-Expiratory Pressure at the Level of the Carina Through the Use of a Novel ITPV Catheter Design, Anesth Analg, 1994, vol. 78, pp. 455-461.

Koopmann, Charles F., et al., Surgical Management of Obstructive Sleep Apnea, Otolaryngologic Clinics of North America, vol. 23, No. 4, Aug. 1990, pp. 787-808.

Krachman, S. L., et al., Comparison of oxygen therapy with nasal continuous positive airway pressure on Cheyne-Stokes respiration during sleep in congestive heart failure, Chest, Dec. 1999, vol. 116, No. 6, pp. 1550-1557, abstract.

Kribbs, Nancy Barone, et al., Effects of One Night without Nasal CPAP Treatment on Sleep and Sleepiness in Patients with Obstructive Sleep Apnea, Amercian Review Respiratory Disease, vol. 147, pp. 1162-1168, 1993.

Kribbs, Nancy Barone, et al., Objective Management of Patterns of Nasal CPAP Use by Patients with Obstructive Sleep Apnea, American Review Respiratory Disease, vol. 147, pp. 887-895, 1993.

Krieger, Jean, et al., Breathing During Sleep in Normal Middle-Aged Subjects, Sleep, vol. 13, No. 2, pp 143-154, Raven Press, Ltd. New York, NY, USA, 1990 Association of Professional Sleep Societies.

Krieger, Jean., et al., Dangerous Hypoxaemia During Continuous Positive Airway Pressure Treatment of Obstructive Sleep Apnoea, The Lancet, Dec. 17, 1983, pp. 1429-1430.

Krieger, Jean, et al., Left Ventricular Ejection Fraction in Obstructive Sleep Apnea, Effects of Long-term Treatment with Nasal Continuous Positive Airway Pressure, Chest, vol. 100, No. 4, Oct. 1991, pp. 917-921.

Kuna, S. T., et al., Pathophysiology of upper airway closure during sleep, JAMA, Sep. 11, 1991, vol. 266, No. 10, pp. 1384-1389, abstract.

Kyzer, S., et al., Obstructive Sleep Apnea in the obese, World Journal Surg, Sep. 1988, vol. 22, No. 9, pp. 998-1001, abstract.

Lafontaine, Victoria M., et al., Pulse Oximetry: Accuracy of Methods of Interpreting Graphic Summaries, Pediatric Pulmonology, vol. 21, 1996, pp. 121-131.

Lanfranchi, P. A., et al., Prognostic value of nocturnal Cheyne-Stokes respiration in chronic heart failure, Circulation, Mar. 23, 1999, vol. 99, No. 11, pp. 1435-1440, Italy, abstract.

Lanfranchi, P., et al., The assessment of breathng during sleep: a curiosity or clinical necessity?, Italian Heart Journal, May 2000, vol. 1, No. 5, Suppl., pp. 641-654, abstract.

Lawrence, Nancy, Treatment for Sleep Apnea shows promise in reducing deaths from congestive heart failure: Nation-wide study to determine long-term benefits, London Health Sciences Centre, Jun. 3, 1999, News Bulletin.

Lertzman, Morley, et al., [Letters—Correspondence], Sleep Apnea A Risk Factor for Poor Driving, Canadian Medical Association Journal, Oct. 15, 1995; vol. 153(8), p. 1063.

Letters, Obstructive Sleep Apnoea, BMJ, 1997, pp. 315-367, Aug. 9; http://bmj.com/Shneerson et al. (7104).

Lichstein, K. L., et al., Occult sleep apnea in a recruited sample of older adults with insomnia, Journal of Consulting & Clinical Psychology, vol. 67, No. 3, pp. 405-410, Jun. 1999, abstract.

Little, S. A., et al., Predictors of nocturnal oxygen desaturation in patients with COPD, Respir Med., Mar. 1999, vol. 93, No. 3, pp. 202-207, United Kingdom, abstract.

Lofsky, Ann, Sleep Apnea and Narcotic Postoperative Pain Medication: A Morbidity and Mortality Risk, APSF Newsletter Summer 2002, pp. 24-25.

Longobardo, G. S., et al., Sleep Apnea Considered As A Control System Instability, Elsevier Biomedical Press, 1982, 0034-5687/82/0000-0000.

Lowton, K., Pulse oximeters for the detection of hypoxaemia, Professional Nurse, Feb. 1999, vol. 14, No. 5, pp. 343-347, abstract.

Lugaresi, E., et al., Breathing During sleep in Man in Normal and Pathological Conditions, Proceedings of the Symposium on Regulation of Respiration during Sleep and Anesthesia held at the Faculte de Medecine Saint-Antoine, Paris, France, Jul. 14-16, 1977, 1978 Plenum Press, New York, USA, pp. 35-45.

Lynn, Lawrence A. et al., Diagnostic Evaluation of OSA Utilizing Analysis of Frequency and Spatial Relationships of Clustered, Sequential Oximetry Waveform Events, Vth World Congress on Sleep Apnea, Marburg, Germany, Sep. 17-20, 1997.

Lynn, Lawrence A., Interpretive Oximetry: Future Directons for Diagnostic Applications of the $SpO_2$ Time-Series, Anesth Analg 2002, vol. 94, pp. S84-S88.

Lynn, Lawrence, PROFOX Associates, Inc., Version 12S (12 hours SpO2), Demonstration disk for Dr. Lawrence Lynn, Columbus, Ohio, Copyright 1986 PROFOX Associates, Inc., Version 12S, Nov. 1992, p. 1.

Lyznicki, James M., Sleepiness, Driving and Motor Vehicle Crashes, JAMA, Jun. 17, 1998, vol. 279, No. 23, pp. 1908-1913.

Magalang, Ulysses J. et al., Prediction of the Apnea-Hypopnea Index From Overnight Pulse Oximetry, Chest the Cardiopulmonary and Critical Care Journal, 2003; vol. 124; pp. 1694-1701, Northbrook, IL, USA.

Marin, Jose M., et al., Long-Term Cardiovascular Outcomes in Men with Obstructive sleep apnoea-hypopnoea with or without treatment with continuous positive airway pressure: an observational study, The Lancet, vol. 365, Issue 9464, Mar. 19, 2005-Mar. 25, 2005, pp. 1046-1053.

Marin, Joé M., et al., Obstructive Sleep Apnea and Acute Myocardial Infarction: Clinical Implications of the Association, Sleep, vol. 21, No. 8, 1998, pp. 809-815.

Mayer, Pierre, et al., Peripheral Neuropathy in Sleep Apnea, A Tissue Marker of the Severity of Nocturnal Desaturation, American Journal Respiratory Critical Care Medicine, vol. 159, pp. 213-219, 1999, Internet address: www.atsjournals.org.

McDannold, M. D., et al., Night-to-Night variability in Optimal CPAP Pressures Using Auto CPAP Titration in a Single Patient, Sleep Research No. 23, 1994, p. 453, abstract.

McEvoy, R. D., et al., Ventilatory responses to sustained eucapnic hypoxia in healthy males during wakefulness and NREM sleep, Sleep, vol. 20, No. 11, Nov. 1997, pp. 1008-1011, abstract.

McGregor, Christine D. et al., Performance of Pulse Oximeter Technologies in A Pediatric Sleep Lab Setting, OF-901-191, dated Nov. 2, 2001, abstract.

McNicholas, W. T., et al., Diagnostic Criteria for the Sleep Apnoea Syndrome: Time for Consensus?, European Respiratory Journal, vol. 9, pp. 634-635, 1996, United Kingdom.

Mehra, Reena, et al., Association of Nocturnal Arrhythmias with Sleep Disordered Breathing: The Sleep Heart Health Study, AJRCCM Articles in Press, Published Jan. 19, 2006, as doi: 10.1164/rccm.200509-1442OC, Copyright 2006 by the American Thoracic Society.

Mehta, Y., et al., Obstructive sleep apnea syndrome: anesthetic implications in the cardiac surgical patient, Journal Cardiothorac Vasc Anesth, Aug. 2000, vol. 14, No. 4, pp. 449-453, abstract.

Mendelson, W. B., et al., Effects of Hemodialysis on Sleep Apnea Syndrome in End-Stage Renal Disease, Clinical Nephrology, vol. 33, No. 5, 1990, pp. 247-251.

Middlekoop, Huub, et al., The Value of Nocturnal Motor Activity Monitoring as a Screening Tool for Obstructive Sleep Apnoea, Letter to the Editor, Journal Sleep Res., 1996, vol. 5, pp. 66-67.

Miles, L. E., et al., Development and Application of Automatic Nasal CPAP Calibration Procedures for Use in the Unsupervised Home Environment, Sleep, vol. 16, pp. S118-S119, 1993 American Sleep Disorders Association and Sleep Research Society.

Miles, Laughton E., Optimization of Nasal-CPAP Airflow Pressure by Use of Home Oximetry Recordings, Clinical Monitoring Center, Palo Alto, California, USA, Sleep Research, p. 568, 1987, abstract.

Millard, R. K., Inductive plethysmography components analysis and improved noninvasive postoperative apnoea monitoring, Physiol Meas, May 1999, vol. 20, No. 2, pp. 175-186, United Kingdom, abstract.

Mitler, Merrill M., et al., Narcolepsy and Its Treatment With Stimulants, ASDA Standards of Practice, Sleep, vol. 17, No. 4, pp. 352-371, 1994, American Sleep Disorders Association and Sleep Research Society.

Miyamura, Miharu, et al., $CO_2$ Dissociation Curves of Oxygenerated Whole Blood Obtained at Rest and in Exercise, European Journal Applied Physiology, vol. 39, pp. 37-45, 1978, European Journal of Applied Physiology and Occupation Physiology.

Morelot-Panzini, Capucine et al., Simplified Method to Measure Respiratory-Related Changes in Arterial Pulse Pressure in Patients Receiving Mechanical Ventilation, Chest 2003, vol. 124, pp. 665-670, Northbrook, IL, USA.

Muller, Nestor L., et al., Mechanism of Hemoglobin Desaturation During Rapid-Eye-Movement Sleep in Normal Subjects and in Patients with Cystic Fibrosis, American Review of Respiratory Disease, vol. 121, 1980, pp. 463-469.

Myatt, H. M., et al., Snoring—a simple surgical solution, Clin. Otolaryngol., 1996, vol. 21, pp. 419-424, Publisher: Blackwell Science Ltd.

Narkiewicz, Krzysztof, et al., Altered Cardiovascular Variability in Obstructive Sleep Apnea, Copyright 1998, American Heart Association, Inc., Iowa City, Iowa, USA, pp. 1071-1077, Published Sep. 15, 1998.

Naughton, Matthew T., Cycling Sleep Apnea, The Balance of Compensated and Decompensated Breathing, American Journal of Respiratory and Critical Care Medicine, vol. 168, 2003, Editorials, pp. 624-625.

Naughton, Matthew T., et al., Sleep Apnea in Congestive Heart Failure, Clinics in Chest Medicine, vol. 19, No. 1, Mar. 1998, pp. 99-113.

Netzer, Nikolaus, et al., Overnight Pulse Oximetry for Sleep-Disordered Breathing in Adults, A Review, Chest, vol. 120, #2, Aug. 2001, pp. 625-633, Northbrook, IL, USA.

Neumann, Christina et al., Nocturnal oxygen desaturation in diabetic patients with severe autonomic neuropathy, Diabetes Research and Clinical Practice, Publisher: Elsevier Science Ireland Ltd, vol. 28, 1995, pp. 97-102.

Nobili, L., et al., Morning increase of whole blood viscosity in obstructive sleep apnea syndrome, Clinical Hemorheol Microcirc, 2000, vol. 22, No. 1, pp. 21-27, abstract.

Noda, A., et al., Daytime sleepiness and automobile accidents in patients with obstructive sleep apnea syndrome, Psychiatry & Clinical Neurosciences, vol. 52, No. 2, pp. 221-222, Apr. 1988, abstract.

Noda, Akiko, et al., Circadian Rhythm of Autonomic Activity in Patients with Obstructive Sleep Apnea Syndrome, Clinical Cardiology, vol. 21, pp. 271-276, 1998, Japan.

Ogan, O. U., et al., Anesthetic safety always an issue with obstructive sleep apnea, Journal Clin Monit Comput, Jan. 1998, vol. 14, No. 1, pp. 69-70, abstract.

Ogretmenoglu, O., et al., Body fat composition: a predictive factor for obstructive sleep apnea, Laryngoscope, Aug. 2005, vol. 115, No. 8, pp. 1493-1498, abstract.

Ohga, Eijiro, et al., Increased Levels of Circulating ICAM-1, VCAM-1, and L-selectin in obstructive sleep apnea syndrome, Address for reprint requests and other correspondence: T. Nagase, Dept. of Geriatric Medicine, Faculty of Medicine, Univ. of Tokyo, 7-3-1, Hongo, Bunkyo-Ku, Tokyo 113, Japan, Received Nov. 13, 1998, accepted in final form Mar. 9, 1999.

Olson, L. G., et al., Prediction of Sleep-disordered breathing by unattended overnight oximetry, Journal Sleep Res., 1999, vol. 8, pp. 51-55, European Sleep Research Society.

Olson, Leslie G., et al., Chapter 10, A Biomechanical View of Upper Airway Function, pp. 359-389, 1988, Publisher, Marcel Dekker, Inc., New York—Basel, Book: Respiratory Function of the Upper Airway.

Ostermeier, A. M., et al., Three sudden postoperative respiratory arrests associated with epidural opioids in patients with sleep apnea, Anasth Analg., Aug. 1997, vol. 85, No. 2, pp. 452-460.

Owen, G. O., et al., Overnight Pulse Oximetry in Normal Children and in Children Undergoing Adenotonsillecomy, Clinical Otolaryngology, 1996 vol. 21, pp. 59-65, Blackwell Science Ltd.

Owen, G. O., et al., Overnight Pulse Oximetry in Snoring and Non-Snoring Children, Clinical Otolaryngology, 1995, vol. 20, pp. 402-406, Blackwell Science Ltd.

OxiScan, AirSep Corporation, 800/874-0202, Oxiscan Sample Report/Explanation and the Delta Sleep Apnea Index, OxiScan Sample Report, vol. 1, Rev. 01, Nov. 1997.

Pae, E. K., et al., Intermittent hypoxia damages cerebellar cortex and deep nuclei, Neurosci Lett., Feb. 28, 2005, vol. 375, No. 2, pp. 123-128, abstract.

Partinen, Markku et al., Daytime Sleepiness and Vascular Morbidity at Seven-Year Follow-up in Obstructive Sleep Apnea Patients, Chest, vol. 97, No. 1, Jan. 1990, pp. 27-32.

Payne, J. P., Apnoeic Oxygenation in Anaesthetised Man, Acta Anaesth. Scandinav., 1962, vol. 6, pp. 129-142.

Peker, Y., et al., An independent association between obstructive sleep apnoea and coronary artery disease, European Respiratory Journal, 1999, vol. 14, No. 1, pp. 179-184, abstract.

Peker, Y., et al., Reduced hospitalization with cardiovascular and pulmonary disease in obstructive sleep apnea patients on nasal CPAP treatment, Sleep, 1997, vol. 20, No. 8, pp. 45-53, abstract.

Peled, N., et al., Nocturnal ischemic events in patients with obstructive sleep apnea syndrome and ischemic heart disease: effects of continuous positive air pressure treatment, Journal American Coll Cardiology, Nov. 1999, vol. 15, p. 34, abstract.

Pelttari, Lisa H., et al., Little Effect of Ordinary Antihypertensive Therapy on Nocturnal High Blood Pressure in Pateints with Sleep Disordered Breathing, American Journal of Hypertension, 1998, vol. 11, No. 3, Part 1, pp. 272-279.

Penzel, T., et al., Systematic Comparison of Different Algorithms for Apnoea Detection Based on Electrocardiogram Recordings, Medical & Biological Engineering and Computing 2002, vol. 40, pp. 402-407.

Peppard, Paul E., et al., Prospective Study of the Association Between Sleep-Disordered Breathing and Hypertension, May 11, 2000, vol. 342, No. 19, pp. 1378-1384.

Peters, John P. Jr., et al., Studies of the Carbon Dioxide Absorption Curve of Human Blood, Book: The Journal of Biological Chemistry, pp. 709-716, Received for publication, Feb. 7, 1923.

Peters, John P. Jr., et al., The Carbon Dioxide Absorption Curve and Carbon Dioxide Tension of the Blood of Normal Resting Individuals, Book: Carbon Dioxide Absorption Curve, pp. 489-547, Received for publication, Dec. 2, 1920 (missing pp. 490, 491, 538-541).

Phillips, Barbara A., et al., Catching Up On Sleep, The National Sleep Disorders Research Plan, Editorial, Chest, vol. 110, No. 5, Nov. 1996, pp. 1132-1133.

Phillips, Susan, et al., Obstructive Sleep Apnoea: Diagnosis and Management, Nursing Standard, vol. 11, No. 17, pp. 43-46, 1997.

Phillipson, Eliot A., Sleep Apnea—A Major Public Health Problem, Editorials, The New England Journal of Medicine, Editorials, vol. 328, No. 17, pp. 1271-1273, Apr. 29, 1993.

Plastiras, James, Sleep disorders create need for more sleep labs, Capital District Business Review, Mar. 9, 1998.

Poets, C. F., Apparent life-threatening events and sudden infant death on a monitor, Paediatr Respiratory Review, 2004, Suppl. A, pp. S383-S386, abstract.

Poets, C. F., et al., Arterial oxygen saturation and breathing movements during the first year of life, Journal Developmental Physiology, Jun. 1991, vol. 15, No. 6, pp. 341-345, abstract.

Poets, C. F., et al., Home monitoring of transcutaneous oxygen tension in the early detection of hypoxaemia in infants and young children, Arch Dis Child, Jun. 1991, vol. 66, No. 6, pp. 67682, abstract.

Poets, C. F., et al., Patterns of oxygenation during periodic breathing in preterm infants, Early Human Development, Jul. 1991, vol. 26, No. 1, pp. 1-12, abstract.

Poets, C. F., et al., Oxygen saturation and breathing patterns in infancy. 2: Preterm infants at discharge from special care, Arch Dis Child, May 1991, vol. 66, No. 5, pp. 574-578, abstract.

Pradhan, Pratik S., et al., Screening for Obstructive Sleep Apnea in Patients Presenting for Snoring Surgery, Laryngoscope, vol. 106, Nov. 1996, pp. 1393-1397.

Principe-Rodriguez, K., et al., Sleep symptoms and clinical markers of illness in patients with heart failure, Sleep Breath., Sep. 2005, vol. 9, No. 3, pp. 127-133, abstract.

Quinn, S. J., et al., The Differentiation of Snoring Mechanisms Using Sound Analysis, Clinical Otolaryngol., 1996, vol. 21, pp. 119-123, Publisher: Blackwell Science Ltd.

Randerath, Winfried J., et al., Autoadjusting CPAP Therapy Based on Impedance Efficacy, Compliance and Acceptance, American Journal Respiratory Critical Care Medicine, vol. 163, pp. 652-657, 2001, Internet address: www.atsjournals.org.

Rapoport, David M., et al., Reversal of the "Pickwickian Syndrome" by Long-Term Use of Nocturnal Nasal-Airway Pressure, The New England Journal of Medicine, Oct. 7, 1982, vol. 307, No. 15, pp. 931-933.

Rauscher, Helmuth, et al., Computerized Detection of Respiratory Events During Sleep from Rapid Increases in Oxyhemoglobin Saturation, Lung, 1991, vol. 169, pp. 335-342.

Redline, Susan, et al., Hypopnea, a Floating Metric: Implications for Prevalence, Morbidity Estimates, and Case Finding, Sleep, vol. 20, No. 12, pp. 1209-1217.

Redline, Susan, et al., Recognition and Consequences of Obstructive Sleep Apnea Hypopnea Syndrome, Sleep Disorders, Clinics in Chest Medicine, vol. 19, No. 1, Mar. 1998, Cleveland, Ohio, USA, article and abstract.

Reite, Martin, et al., The Use of Polysomnography in the Evaluation of Insomnia, An American Sleep Disorders Association Review, Sleep, vol. 18, No. 1, 1995, pp. 58-70, American Sleep Disorders Association and Sleep Research Society 1995.

Remmers, John E., et al, Nasal Airway Positive Pressure in Patients with Occlusive Sleep Apnea, Methods and Feasibility, American Review Respiratory Disorders, Dec. 1984, vol. 130, No. 6, pp. 1152-1155.

Rennotte, M. T., Epidural opioids and respiratory arrests, Anesth Analg., Aug. 1997, vol. 85, No. 2, pp. 452-460, abstract.

Resta, O., et al., Sleep-related breathing disorders in acute respiratory failure assisted by non-invasive ventilatory treatment: utility of portable polysomnographic system, Respir Medicine, Feb. 2000, vol. 94, No. 2, pp. 128-134, abstract.

Riley, Robert W., et al., Maxillofacial Surgery and Nasal CPAP, A Comparison of Treatment for Obstructive Sleep Apnea Syndrome, Chest, vol. 98, No. 6, Dec. 1990, pp. 1421-1425.

Riley, Robert W., et al., Maxillofacial Surgery and Obstructive Sleep Apnea: A Review of 80 Patients, Otolaryngology—Head and Neck Surgery, vol. 101, No. 3, Sep. 1989, pp. 353-361.

Riley, Robert W., et al., Maxillofacial Surgery and Obstructive Sleep Apnea Syndrome, Otolaryngologic Clinics of North America, vol. 23, No. 4, Aug. 1990, pp. 809-824.

Rosenberg, J., et al., Ventilatory Pattern and Associated Episodic Hypoxaemia in the Late Postoperative Period in the General Surgical Ward, Anaesthesia, 1999, vol. 54, pp. 323-328, Publisher: Blackwell Science Ltd.

Roux, Francoise, et al., Sleep-related Breathing Disorders and Cardiovascular Disease, The American Journal of Medicine, Apr. 1, 2000, vol. 108, pp. 396-400.

Ruchala, Joanna B., Chapter 13, Applications of Pulse Oximetry, Book: Design of Pulse Oximeters, pp. 214-236.

Ruhle, K. H., et al., Monitoring at Home, Lung, 1990, Suppl, pp. 927-932, Lung, Springer-Verlag, New York, Inc. 1990.

Rundell, O. H., et al., Polysomnography Methods and Interpretations, Sleep Apnea, Otolaryngologic Clinics of North America, vol. 23, No. 4, Aug. 1990, pp. 583-592.

Rusch, T. L., et al., Signal Processing Methods for Pulse Oximetry, Computers in Biology & Medicine, vol. 26, No. 2, pp. 143-159, Mar. 1996, abstract.

Ryan, C. Francis, et al., Mechanical Properties of the Velopharynx in Obese Patients with Obstructive Sleep Apnea, American Journal Respiratory Critical Care Medicine, 1996, vol. 154, pp. 806-812.

Saarelainen, Seppo, et al., Effect of Nasal CPAP Treatment on Plasma Volume, Aldosterone and 24-h Blood Pressure in Obstructive Sleep Apnoea, Journal Sleep Research, 1996, vol. 5, pp. 181-185.

Sadeh, Avi, et al., The Role of Actigraphy in the Evaluation of Sleep Disorders, An American Sleep Disorders Association and Sleep Research Society, Sleep, vol. 18, No. 4, pp. 288-302.

Sadrmoori, Bijan, Evaluation of Self Adjusting Nasal CPAP (DPAP) in the Treatment of Adult Obstructive Sleep Apnea, Sleep Research No. 23, 1994, p. 386, abstract.

Saito, Toshiyuki, et al., Sleep Apnea in Patients with Acute Myocardial Infarction, Critical Care Medicine, vol. 19, No. 7, pp. 938-941, Printed in USA, Copyright 1991 by Williams and Wilkins.

Sajkov, Dimitar, et al., Daytime Pulmonary Hemodynamics in Patients with Obstructive Sleep Apnea without Lung Disease, American Journal Respiratory Critical Care Medicine, 1999, vol. 159, pp. 1518-1526.

Sanders, Mark H., et al., Obstructive Sleep Apnea Treated by Independently Adjusted Inspiratory and Expiratory Positive Airway Pressures via Nasal Mask, Physiologic and Clinical Implcations, Chest, vol. 98, No. 2, Aug. 1990, pp. 317-324.

Sanders, Mark H., Nasal CPAP Effect on Patterns of Sleep Apnea, Chest, vol. 86, No. 6, Dec. 1984, pp. 839-844.

Sangal, R. Bart et al., P300 Latency: Abnormal in Sleep Apnea with Somnolence and Idiopathic Hypersomnia, but Normal in Narcolepsy, Clinical Electroencephalography, 1995, vol. 26, No. 3, pp. 146-153, Troy, Michigan, USA.

Sanna, A., et al., Apport de la Polysomnographie à la mise au point des maladies atteints d'une bronchopneumopathie chronique obstructive (BPCO), Travail Original, Rev. Mèd. Brux., vol. 12, pp. 315-320, 1991, Belgium.

Sanner, B. M., et al., Sleep-related respiration disorders: their relevance in intensive care medicine, [Article in German], Dtsch Med Wochenschr, Mar. 1999, vol. 12, p. 124, abstract.

Sarodia, B.D., et al., Prevalence of obstructive sleep apnea in patients admitted to the intensive care unit with cardiovascular events, Sleep Research, 1996, vol. 25, pp. 356.

Schafer, H., et al., Cardiovascular morbidity in patients with obstructive sleep apnea in relation to the severity of respiratory disorder, Dtsch Med Wochenschr, 1998, vol. 123, No. 39, pp. 1127-1133, abstract.

Schafer, H., et al., Pulmonary Haemodynamics in Obstructive Sleep Apnoea: Time Course and Associated Factors, European Respiratory Journal, 1998, vol. 12, pp. 679-684, Printed in United Kingdom.

Schagatay, E., et al., Diving Response and Apneic Time in Humans, Undersea Hyper Med., 1998, vol. 25, No. 1, pp. 13-19, Copyright 1988 Underseas and Hyperbaric Medical Society, Inc.

Scharf, Martin B., et al., Cyclic Alternating Pattern Sequences in Non-Apneic Snorers With and Without Nasal Dilation, ENT-Ear, Nose & Throat Journal, Sep. 1996, vol. 75, No. 9, pp. 617-619.

Scheers, N. J., et al., Sudden Infant Death With External Airways Covered, Case-Comparison Study of 206 Deaths in the United States, Arch Pediatric Adolescent Medicine, 1998, vol. 152, pp. 540-547.

Schmidt-Notwara, Wolfgang, et al., Oral Appliances for the Treatment of Snoring and Obstructive Sleep Apnea: A Review, An American Sleep Disorders Association Review, Sleep, vol. 18, No. 6, pp. 501-510, 1995, American Sleep Disorders Association and Sleep Research Society.

Schnader, Jeff, Increase of Pulmonary Artery Occlusion Pressure During Upper Airway Obstruction in Sleep Apnea, Case Reports, Critical Care Medicine, 1996, vol. 24, No. 2, pp. 354-358.

Schnapp, Lynn M., et al., Pulse Oximetry Uses and Abuses, Critical Care, Chest, vol. 98, No. 5, Nov. 1990, pp. 1244-1250.

Schneider, H., et al., Neural and local effects of hypoxia on cardiovascular responses to obstructive apnea, Journal Appl Physiol., Mar. 2000, vol. 88, No. 3, pp. 1093-1092, abstract.

Schoenberg, R., et al., Making ICU Alarms Meaningful: A Comparison of Traditional vs. Trend-Based Algorithms, AMIA 1999, Annual Symposium, abstract.

Schwab, Richard J., et al., Upper Airway and Soft Tissue Structural Changes Induced by CPAP in Normal Subjects, American Journal Respiratory Critical Care Medicine, 1996, vol. 154, pp. 1106-1116.

Senn, Oliver, et al., Monitoring Carbon Dioxide Tension and Arterial Oxygen Saturation by a Single Earlobe Sensor in Patients With Critical Illness or Sleep Apnea, Chest 2005, vol. 128, pp. 1291-1296, Northbrook, IL, USA.

Series, Frederic, et al., Prospective Evaluation of Nocturnal Oximetry for Detection of Sleep-Related Breathing Disturbances in Patients With Chronic Heart Failure, Chest 2005, vol. 127, pp. 1507-1514, Northbrook, IL, USA.

Severinghaus, John W., et al., Recent Developments in Pulse Oximetry, Anesthesiology, vol. 76, pp. 1018-1038, 1992.

Shamir, M., et al., Pulse oximetry plethsymographic waveform during changes in blood volume, British Journal of Anaesthesia, vol. 82(2), pp. 178-181, 1999, Great Britian.

Shephard, John W. Jr., et al., Relationship of Ventricular Ectopy to Oxyhemoglobin Desaturation in Patients with Obstructive Sleep Apnea, Chest, vol. 88, No. 3, Sep. 1985, pp. 335-340, Northbrook, IL, USA.

Shephard, John W., Jr., et al., Uvulopalatopharyngoplasty for Treatment of Obstructive Sleep Apnea, Mayo Clinic Proceedings, vol. 65, pp. 1260-1267, 1990.

Sher, Aaron E., et al., The Efficacy of Surgical Modifications of the Upper Airway in Adults With Obstructive Sleep Apnea Syndrome, An American Sleep Disorders Association Review, Sleep, vol. 19, No. 2, pp. 156-177, Nov. 1995.

Shinohara, E., et al., Visceral Fat Accumulation as an Important Risk Factor for Obstructive Sleep Apnoea Syndrome in Obese Subjects, Journal of Internal Medicine, vol. 241, pp. 11-18, Publisher: Blackwell Science Ltd., 1997.

Silverberg, D. S., et al., Essential and Secondary Hypertension and Sleep-Disordered Breathing: A Unifying Hypothesis, Journal of Human Hypertension, 1996, vol. 10, pp. 353-363.

Silverberg, D., et al., Sleep apnoea and hypertension. Active approach to detection of obstructive sleep apnoea is imperative, BMJ, Jul. 2000, vol. 22, pp. 321, abstract.

Silverberg, Donald, The Joint National Committee on Prevention, Detection, Evaluation, and Treatment of High Blood Pressure and Obstructive Sleep Apnea: Let Their Silence Not Be Matched by the Silence of the Ordinary Physician, Arch Intern Med., Jun. 8, 1998, vol. 158, pp. 1272-1273.

Sin, D. D., et al., Effects of continuous positive airway pressure on cardiovascular outcomes in heart failure patients with and without Cheyne-Stokes respiration, Circulation, Jul. 2000, vol. 102, No. 1, pp. 61-66, abstract.

Skjodt, N. M., et al., Screening for hypothyroidism in sleep apnea, American Journal of Respiratory & Critical Care Medicine, vol. 160, No. 2, pp. 732-735, Aug. 1999, abstract.

Smith, Philip E. M., et al., Hypoxemia During Sleep in Duchenne Muscular Dystrophy, American Review Respiratory Disorders, 1988, vol. 137, pp. 884-888.

Smyth, Edward, et al., Apneic Oxygenation Associated with Patient-Controlled Analgesia, Journal of Clinical Anesthesia, vol. 10, pp. 499-501, 1998, Publisher: Elsevier Science, Inc., New York, NY, USA.

Soto, F., Cardiovascular manifestations of obstructive sleep apnea. Effects of the treatment, Rev Med Chil., [Article in Spanish], Sep. 1998, vol. 126, No. 9, pp. 1112-1116, abstract.

Spector, Rosanne, Low-tech Screening for high-risk breathing disorder, http://healthlink.stanford.edu/healthlink/news2/lowtech.thml, Copyright 1996 Stanford University Medical Center News Bureau.

Staniforth, A. D., et al., Nocturnal desaturation in patients with stable heart failure, Heart, Apr. 1998, vol. 79, No. 4, pp. 394-399, United Kingdom, abstract.

Stebbens, V. A., Oxygen saturation and breathing patterns in infancy. 1: Full term infants in the second month of life, Arch Dis Child, May 1991, vol. 66, No. 5, pp. 569-573, abstract.

Stegman, S. S., et al., Asymptomatic bradyarrhythmias as a marker for sleep apnea: appropriate recognition and treatment may reduce the need for pacemaker therapy, Pacing Clin Electrophysiol, Jun. 1996, vol. 19, No. 6, pp. 899-904, abstract.

Stradling, J. R., et al., Automatic Nasal Continuous Positive Airway Pressure Titration in the Laboratory: Patient Outcomes, Thorax, 1997, vol. 52, pp. 72-75.

Stradling, J. R., et al., Predictors and Prevalence of Obstructive Sleep Apnoea and Snoring in 1001 Middle Aged Men, Thorax, 1991, vol. 46, pp. 85-90.

Stradling, John R., et al., Relation between systemic hypertension and sleep hypoxaemia or snoring: analysis in 748 men drawn from general practice, BMJ, vol. 300, Jan. 13, 1990, pp. 75-78.

Strohl, Kingman P., Consequences of Sleep-Disordered Breathing, Respiratory Care, Apr. 1998, vol. 43, No. 4, pp. 277-282.

Strohl, Kingman P., et al., Physiologic Basis of Therapy for Sleep Apnea, State of Art: Physiologic Basis of Therapy for Sleep Apnea, pp. 791-802.

Sullivan, Colin E., et al., Reversal of Obstructive Sleep Apnoea by Continuous Positive Airway Pressure applied through the Nares, The Lancet, Apr. 18, 1981, pp. 862-865.

Sullivan, Mary Anna et al., PCA Update, Unexpected Deaths of Patients Receiving Patient-Controlled Analgesia, Nov. 2001.

Svatikova, A., et al., Plasma brain natriuretic peptide in obstructive sleep apnea, American Journal Cardiology, Aug. 15, 2004, vol. 94, No. 4, pp. 529-532, abstract.

Szaboova, E., et al., Obstructive Sleep Apnea as a Cause of Dysrhythmia in Sudden Cardiac Death, Bratisl Lek Listy, Jul.-Aug. 1997, vol. 98, Nos. 7-8, pp. 448-453, abstract.

Tanchaiswad, Waran, Is Sudden Unexplained Nocturnal Death a Breathing Disorder?, Review Article, Psychiatry and Clinical Neurosciences, 1995, vol. 49, pp. 111-114.

Tanigawa, T., et al., Screening for sleep-disordered breathing at workplaces, Ind. Health, Jan. 2005, vol. 43, No. 1, pp. 53-57, abstract.

Teramoto, S., et al., Does the altered cardiovascular variability associated with obstructive sleep apnea contribute to development of cardiovascular disease in patients with obstructive sleep apnea syndrome?, Circulation, Dec. 21, 1999, vol. 100, No. 25, pp. e136-e137, abstract.

Teschler, H., et al., Influence of Moderate Alcohol Consumption on Obstructive Sleep Apnoea with and without AutoSet™ Nasal CPAP Therapy, European Respiratory Journal, 1996, vol. 9, pp. 2371-2377, Printed in United Kingdom.

Teschler, Helmut, et al., Automated Continuous Positive Airway Pressure Titration for Obstructive Sleep Apnea Syndrome, American Journal Respiratory Critical Care Medicine, vol. 154, pp. 734-740, 1996.

The American Sleep Disorders Association Accreditation Committee, Standards for Accreditation of Sleep Disorders Centers, American Sleep Disorders Association, Rochester, MN, Mar. 1997, Revised Edition, pp. 1-17 (p. 16 missing).

Thorpy, Michael J., The Clinical Use of the Multiple Sleep Latency Test, Report From the American sleep Disorders Association, Sleep, vol. 15, No. 3, 1992, pp. 268-276, American Sleep Disorders Association and Sleep Research Society.

Thorpy, Michael, et al., ASDA Standards of Practice, Practice Parameters for the Use of Portable Recording in the Assessment of Obstructive Sleep Apnea, Standards of Practice Committee of the American Sleep Disorders Associate, Sleep, vol. 17, No. 4, pp. 372-377.

Thorpy, Michael, et al., Practice Parameters for the Treatment of Obstructive Sleep Apnea in Adults: The Efficacy of Surgical Modifications of the Upper Airway, An American Sleep Disorders Association Review, Sleep, vol. 19, No. 2, pp. 152-155, 1996, American Sleep Disorders Association and Sleep Research Society.

Thorpy, Michael, et al., Practice Parameters for the Treatment of Snoring and Obstructive Sleep Apnea with Oral Appliances, An American Sleep Disorders Association and Sleep Research Society, Sleep, vol. 18, No. 6, pp. 511-513, 1995.

Thorpy, Michael, et al., Practice Parameters for the Use of Actigraphy in the Clinical Assessment of Sleep Disorders, An American Sleep Disorders Association Report, Sleep, vol. 18, No. 4, pp. 285-287, 1995 American Sleep Disorders Association and Sleep Research Society.

Thorpy, Michael, et al., Practice Parameters for the Use of Laser-assisted Uvulopalatoplasty, An American Sleep Disorders Association and Sleep Research Society, Sleep, vol. 17, No. 8, pp. 744-748, 1994.

Thorpy, Michael, et al., Practice Parameters for the Use of Polysomnography in the Evaluation of Insomnia, An American Sleep Disorders Association Report, Sleep, vol 18, No. 1, pp. 55-57, 1995 American Sleep Disorders Association and Sleep Research Society.

Tkacova, R., et al., Continuous positive airway pressure improves nocturnal barareflex sensitivity of patients with heart failure and obstructive sleep apnea., Journal Hypertension, Sep. 2000, vol. 18, No. 9, pp. 1257-1262, abstract.

Tkacova, R., et al., Effects of continuous positive airway pressure on obstructive sleep apnea and left ventricular afterload in patients with heart failure, Circulation, 1998, vol. 98, No. 21, pp. 2269-2275, abstract.

Tobert, Daren G., et al., Laboratory Medicine and Pathology, New Directions for Pulse Oximetry in Sleep Disorders, Mayo Clinic Proceedings, 1995, vol. 70, pp. 591, Rochester, Minnesota, USA.

Tobin, Martin J., et al., Breathing Abnormalaties During Sleep, Arch Intern Med, vol. 143, Jun. 1983, pp. 1221-1228.

Trang, H., et al., [B20] [Poster: 904] Masimo SetR Pulse Oximetry Improves Detection Of Sleep Apnea-Related Hypoxemia, Nov. 2, 2001, C:/Masimo/Biblio, page 1 of 1.

Tremel, F., et al., High prevalence and persistence of sleep apnoea in patients referred for acute left ventricular failure and medically treated over 2 months, European Heart Journal, Aug. 1999, vol. 20, No. 16, pp. 120-129.

Trinder, J., et al., Pathiophysiological interactions of ventilation, arousals, and blood pressure oscillations during Cheyne-Stokes respiration in patients with heart failure, American Journal Respiratory Critical Care Medicine, Sep. 2000, vol. 162, No. 3 Pt. 1, pp. 808-813, abstract.

Trupp, R. J., et al., Prevalence of sleep disordered breathing in a heart failure program, Congestive Heart Failure, Sep.-Oct. 2004, vol. 10, No. 5, pp. 217-220, abstract.

Trupp, R. J., The heart of sleep: sleep-disordered breathing and heart failure, Journal Cardiovascular Nursing, Nov.-Dec. 2004, vol. 19, No. 6, Suppl, S67-S74, abstract.

Ullmer, E., et al., Cheyne-stokes respiration or obstructive sleep apnoea: patterns of desaturation, Respiration, 2000, vol. 67, No. 2, p. 203, abstract.

VanBoxem, T. J., et al., Prevalence and severity of sleep disordered breathing in a group of morbidly obese patients, Netherlands Journal of Medicine, vol. 54, No. 5, pp. 202-206, May 1999, abstract.

VanSlyke, Donald D., et al., Studies of Gas and Electrolyte Equilibria in Blood, pp. 781-798, Journal Biol. Chem., Oct. 1928, vol. 79, No. 2.

Verbraecken, J., et al., Chronic $CO_2$ Drive in Patients with Obstructive Sleep Apnea and Effect of CPAP, Respiration Physioogy, vol. 101, pp. 279-287, 1995, Publisher: Elsevier.

Vgontzas, Alexandros N., et al., Obesity Without Sleep Apnea Is Associated with Daytime Sleepiness, Arch Intern Med., Jun. 22, 1998, vol. 158, pp. 1333-1337.

Vidhani, K., et al., Obstructive sleep apnoea syndrome: is this an overlooked cause of desaturation in the immediate postoperative period?, Brisith Journal Anaesth, Apr. 1997, vol. 78, No. 4, pp. 442-443, abstract.

Visser, B.F., Pulmonary Diffusion of Carbon Dioxide, Med. Biol. vol. 5, pp. 155-166, Issue 2, Oct. 1960.

Waldhorn, Richard E., Surgical Treatment of Obstructive Sleep Apnea, Is Mandibular Surgery an Advance?, Chest, 1998, vol. 6, Dec. 1990, pp. 1315-1316.

Walker, Regina Paloyan, et al., Uvulopalatopharyngoplasty Versus Laser-Assisted Uvulopalatoplasty for the Treatment of Obstructive Sleep Apnea, Laryngooscope, vol. 107, Jan, 1997, pp. 76-82.

Weber, W., et al., Low-Perfusion Resistant Pulse Oximetry, Abstract Only, Journal of Clinical Monitoring, vol. II, No. 4, Jul. 1995, p. 284.

Weiss, J. Woodrow, et al., Cardiovascular Morbidity in Obstructive Sleep Apnea, Progess in Cardiovascular Diseases, vol. 41, No. 5, Mar./Apr. 1999, pp. 367-376.

Wessendorft, T. E., et al., Sleep-disordered breathing among patients with first-ever stroke, Journal Neurology, Jan. 2000, vol. 247, No. 1, pp. 41-47, abstract only.

West, Peter, et al., Dynamic in Vivo Response Characteristics of Three Oximeters: Hewlett-Packard 47201A, Biox III, and Nellcor N-100, Sleep, vol. 10, No. 3, 1987, pp. 263-271, Raven Press, New York, USA.

Westesson, Per-Lennart, et al., Morbidity after temporomandibular joint arthrography is lower than after removal of lower third molars, Oral Surgery Oral Medical Oral Pathol., 1990, vol. 70, pp. 2-4.

Wheatley, J. R., et al., Mechanical properties of the upper airway, Curr Opin Pulm Medicine, Nov. 1998, vol. 4, No. 6, pp. 363-369, abstract.

White, David P., Pathophysiology of Obstructive Sleep Apnoea, Sleep-Related Breathing Disorder—2, Thorax, 1995, vol. 50, pp. 797-804.

Whitelaw, William A., et al., Clinical Usefulness of Home Oximetry Compared with Polysomnography for Assessment of Sleep Apnea, American Journal Respiratory Critical Care Medicine, vol. 171, pp. 188-193, 2005, Internet address: www.atsjournals.org.

Whitman, R. A., et al., Comparison of the New Masimo SET V3 Technology with a Conventional Pulse Oximeter during Polysomnography, Sleep, 2001, vol. 24, pp. A412 (730.R).

Wiater, A., et al., Polysomnographic Standards for Infants and Childeren, Somnologie, vol. 4, pp. 39-42, 2000, Berlin—Wien.

Wieczorek, Paul M., et al., Obstructive Sleep Apnea Uncovered After High Spiral Anesthesia: A Case Report, Cardiothoracic Anesthesia, Respiration and Airway, Canadian Journal of Anesthesia, 2005, vol. 52, No. 7, pp. 761-764.

Wilhoit, Stephen C., et al., Comparison of Indices Used to Detect Hypoventilation during Sleep, Respiration, vol. 47, pp. 237-242; 1985.

Williams, Adrian J., et al., Clinical Value of Polysomnography, The Lancet, vol. 339, May 2, 1992, p. 1113.

Wright, John, et al., Health effects of obstructive sleep apnoea and the effectiveness of continuous positive airways pressure: a systematic review of the research evidence, BMJ, vol. 314, Mar. 22, 1997, pp. 851-860.

Wright, John, et al., Letters, Obstructive Sleep Apnoea, Authors' reply, bmj.com, Jun. 26, 2001.

Wynne, James W., et al., Disordered Breathing and Oxygen Desaturation During Sleep in Patients with Chronic Obstructive Lung Disease (COLD), The American Journal of Medicine, vol. 66, Apr. 1979, pp. 573-579.

Yamakage, M., et al., Changes in respiratory pattern and arterial blood gases during sedation with propofol or midazolam in spinal anesthesia, Journal Clinical Anesth, Aug. 1999, vol. 11, No. 5, pp. 375-379, abstract.

Yantis, M. A., Decreasing surgical risks for patients with obstructive sleep apnea, AORN Journal, Jul. 1998, vol. 68, No. 1, pp. 50-55, abstract.

Younes, Magdy, et al., Chemical Control Stability in Patients with Obstructive SleepApnea, American Journal Respiratory Critical Care Medicine, vol. 163, pp. 1181-1190, 2001.

Young, Terry, et al., The Gender Bias in Sleep Apnea Diagnosis, Are Women Missed Because They Have Different Symptoms?, Original Investigation, Arch Intern Medicine, vol. 156, Nov. 25, 1996, pp. 2445-2451.

Zafar, Subooha, et al., Choice of Oximeter Affects Apnea-Hypopnea Index, Chest, vol. 127/1, Jan. 2005, pp. 80-88, Clinical Investigations, www.chestjournal.org.

Zamarron, C., et al., Oximetry Spectral Analysis in the Diagnosis of Obstructive Sleep Apnoea, Clinical Science, 1999, vol. 97, pp. 467-473, Printed in Great Britain.

Zoccali, Carmine, et al., Nocturnal Hypoxemia, Night-Day Arterial Pressure Changes and Left Ventricular Geometry in Dialysis Patients, Kidney International, vol. 53, 1998, pp. 1078-1084, International Society of Nephrology.

Zou, Ding, et al., Obstructive Apneic Events Induce Alpha-Receptor Mediated Digital Vasoconstriction, Sleep, vol. 27, No. 3, 2004, pp. 485-489.

Zucconi, M., et al., An unattended device for sleep-related breathing disorders: validation study in suspected obstructive sleep apnoea syndrome, European Respiratory Journal, 1996, vol. 9, pp. 1251-1256, Printed in United Kingdom.

Downs, John B., Has Oxygen Administration Delayed Appropriate Respiratory Care? Fallacies Regarding Oxygen Therapy, Respiratory Care, Jun. 2003, vol. 48, No. 6.

Downs, John B., Is Supplemental Oxygen Necessary, Journal of Cardiothoracic and Vascular Anesthesia, vol. 20, No. 2, Apr. 2006.

Fu, Eugene S., et al., Supplemental Oxygen Impairs Detection of Hypoventilation by Pulse Oximetry, Chest 2004; vol. 126, pp. 1552-1558.

* cited by examiner

*Primary Examiner*—Eric F Winakur
(74) *Attorney, Agent, or Firm*—Fletcher Yoder

(57) ABSTRACT

A relational pulse oximetry alarm system and method is presented for earlier identification of the occurrence of an adverse clinical event. The system includes a pulse oximeter based microprocessor alarm system which provides an alarm based on a relational conformation of a plurality of time series and further based on the recognition of specific dynamic patterns of interaction between a plurality of corresponding and related time series including the occurrence of pathophysiologic divergence of two or more time series outputs. The processor is programmed to compare a first time series to a second time series to produce a comparison result, to identify a relationship between the first time series and the second time series, to identify a relational threshold breach, and to output an alarm based on the relational threshold breach. The system can include an oximeter testing system for predicting the timeliness of the response of the alarm of a pulse oximeter to the occurrence of an adverse clinical event.

44 Claims, 3 Drawing Sheets

PULSE OXIMETRY RELATIONAL ALARM SYSTEM FOR EARLY RECOGNITION OF INSTABILITY AND CATASTROPHIC OCCURRENCES

This application is a continuation of U.S. application Ser. No. 10/162,466, filed Jun. 3, 2002, now abandoned, which claims the benefit of provisional application No. 60/295,484, filed Jun. 1, 2002, which is incorporated by reference in its entirety as if completely disclosed herein. This application and Ser. No. 10/162,466 are continuations-in-part of application Ser. No. 10/150,582, filed May 17, 2002, now U.S. Pat. No. 7,081,095, which is incorporated herein by reference, and which claims the benefit of provisional applications Nos. 60/291,687 and 60/291,691 filed on May 17, 2001 (both of which are also incorporated herein by reference). The present application and Ser. No. 10/162,466 are also continuations-in-part of U.S. application Ser. No. 10/150,842, filed May 17, 2002, currently pending, which also claims the benefit of aforesaid provisional applications Nos. 60/291,687 and 60/291,691. U.S. application Ser. No. 10/162,466 is also a continuation-in-part of U.S. application Ser. No. 10/132,535, filed Apr. 24, 2002, now U.S. Pat. No. 6,748,252, which is a division of U.S. application Ser. No. 09/776,771, filed Feb. 6, 2001, now U.S. Pat. No. 6,760,608, which is a continuation of U.S. application Ser. No. 09/115,226, filed Jul. 14, 1998, now U.S. Pat. No. 6,223,064, which claims the benefit of provisional applications Nos. 60/052,438 and 60/052,439, filed on Jul. 14, 1997.

FIELD OF THE INVENTION

This application relates to improved alarm systems for oximetry and to methods of relational signal processing to enhance the specificity and timeliness of the alarms of pulse oximeters.

BACKGROUND AND SUMMARY OF THE INVENTION

Delay in recognition of respiratory instability and and/or arrest is a very common cause of unexpected death in the US hospitals. Many adverse reactions to medication and complications of surgery cause death by inducing respiratory arrest, which must be recognized early if death is to be reasonably prevented. In addition most serious diseases, such as, for example, stroke, pneumonia, blood born infections and urinary infections ultimately cause death by progression to respiratory arrest and this progression can occur very suddenly. The period of respiratory instability preceding respiratory arrest is highly variable ranging from more than 24 hours to less than a minute. Respiratory instability is painless and generally causes shortness of breath, which is often discounted by hospital personnel since this symptom is so common patients in the hospital. For these reasons the significance of the warning symptoms and signs of impending respiratory arrest are often missed by physicians and nurses since the symptoms are thought to simply be due to, for example, anxiety, postoperative pain, or fever.

It has long been known that, if patient survival is to be reasonably achieved, respiratory arrest must be reversed very quickly—before it progresses to cardiac arrest. In many cases respiratory arrest can be readily reversed and the patient stabilized by a simple bag and mask or even simple mouth to mouth resuscitation. However, once respiratory arrest induces cardiac arrest chest compressions and cardiopulmonary resuscitation becomes necessary and the success of such resuscitation in this setting is very low. The progression of respiratory arrest to cardiac arrest is perhaps best termed as a state of "dual (oxygen depletion) arrest".

To compare the significance of dual arrest it is important to contrast the process of sudden cardiac arrest as the primary event with that of a sudden primary respiratory arrest. In contrast with the dual arrest state described above, oxygen stores in arteries, veins, and lungs are retained after a sudden cardiac arrest. If the heart can be restarted (which can often be achieved within seconds by defibrillation) these oxygen stores are immediately available to restore oxygen to the brain and heart muscle and normal ventilation generally spontaneously returns. If on the other hand a respiratory arrest is the initial event, the body oxygen stores are depleted as the heart pumps the remaining oxygen stores to keep the brain and heart muscle alive after the cessation of breathing. (The heart rate generally slows during this period to reduce the use of oxygen be the heart muscle). When the oxygen stores are depleted the heart muscle stops contracting or cardiac electrical instability develops producing a secondary cardiac arrest the state of dual arrest. Upon progression to the state of dual arrest the restarting of only one system (heart or lungs) will not induce survival. Both must be restarted and this takes much more time and is much less successful. For example once dual arrest occurs, the simple restarting of the heart (as with defibrillation), will be generally unsuccessful (and useless in any regard), since the oxygen within the body has been depleted and the pumping of blood will not restore oxygen to the brain or heart muscle or restore spontaneous breathing (as would occur if the cardiac arrest was primary). In addition after dual arrest has occurred ventilating the simple ventilation of the patient, which might have easily saved the life of the patient, only seconds earlier will now be useless if not combined with complicated and often poorly successful cardiac resuscitation maneuvers.

Patients who are pregnant, obese, or have heart or lung disease may have lower oxygen stores at the time of the respiratory arrest. This means that depletion and progression to dual arrest can occur very rapidly in these patients. To understand the critical limitation of time between the onset of respiratory arrest and the development of dual arrest due to oxygen depletion in the real world, consider the case of respiratory arrest (as, for example, due to an adverse drug reaction) of a mother at near term pregnancy. After the respiratory arrest both the baby and the mother are rapidly depleting the mother's oxygen stores (which is already low due to the reduced size of the lungs due to size of the full term baby). Both the low oxygen stores and the more rapid depletion of those stores can greatly shorten the time to dual arrest, an occurrence which, if not prevented by timely ventilation, would likely result in death of both the mother and the baby. Here it can be seen that the time between the onset of the respiratory arrest and the sounding of the alarm is pivotal toward determining whether the mother and baby can be saved by simple ventilation or subjected to complex and commonly unsuccessful CPR.

Upon the recognition that it was actually respiratory arrest, which was the major leading cause of unexpected death in the hospital, the monitoring companies began to enhance electrocardiographic (EKG) monitors by combining them with pulse oximetry so both adverse cardiac events and adverse respiratory events could be identified. Today, telemetry and bedside monitors with both pulse oximetery and EKG are in wide use on hospital wards as early warning devices. Unfortunately while the alarm systems of the EKG components of the multimode monitors are excellent for immediately identifying cardiac arrest, the alarms of the incorporated pulse oximeters are very poorly suited for early identification of respiratory arrest, and in the present art these devices provide a false sense of security because they alarm in response to a respiratory arrest only after a prolonged delay—a point wherein progression to dual arrest is very near. For these reasons, a patient experiencing a respiratory arrest on a telemetry ward in US hospitals today, even though monitored by combined telemetry EKG and pulse oximetry, has a high probability of progressing to dual arrest before simple respiratory arrest is identified and reversed.

The occurrence of important delays in oximeter detection of critical clinical events has been known for many years (see "Delayed detection of hypoxic events by pulse oximeters: computer simulations", Verhoeff F, Sykes M. K. Anaesthesia February 1990; 45(2):103-9). One of the factors contributing to this delay has been the high false alarm rate of pulse oximeters. Pulse oximeters have traditionally produced an output, which can be affected by motion and other sources of artifact. U.S. Pat. No. 6,206,830 entitled "signal processing apparatus and method", the contents of which is incorporated by reference as if completely disclosed herein, provides background for some of the deficiencies associated with the present art of monitoring patients using pulse oximetry. To address these deficiencies, in the present art, the output signal is subjected to a wide range of signal processing including different filters such as low pass and averaging filters as well as adaptive filters. These filters, while reducing false alarms, may significantly decrease the dynamic response of the oximeter so that the true alarm may be delayed. Since, as noted, pulse oximeters are now being coupled with telemetry units for transmission of the oxygen saturation values to a central station the transmission may be intermittent (for example to save battery power) with the central station updated only at predetermined intervals. This can result in an additional delay. Each of these delays can be additive and this can seriously reduce the remaining time available to hospital personnel after the alarm to reverse the respiratory arrest before the onset of the much less reversible dual arrest state.

Since thousands of patients die every year from delayed recognition of respiratory arrest, scientists in the field of pulse oximetry have been working hard to improve patient monitoring in this environment. Much of the work has focused on the adverse effect induced by excessive false alarms on the timeliness of the response to a true alarm. In response manufacturers have provided selectable delays with some pulse oximeters to reduce the number of false alarms, but the disclosed methods reduce false alarms by producing a further delay in response to true alarms. U.S. Pat. No. 5,865,763 entitled, "Method and apparatus for nuisance alarm reductions" (the disclosure of which is incorporated by reference as if completely disclosed herein) shows one such selectable delay system and provides additional background for the present invention.

However, since the delay in the disclosed method and apparatus which mitigates false alarms also results in a delay in alarm response to a respiratory arrest, this new alarm system reduces false alarms at the expense of providing less time to prevent progression to the highly fatal state of dual arrest.

When monitored by the basic conventional hospital montage (which includes electrocardiogram, pulse oximetry, and chest wall impedance, EKG), the human physiologic system produces a large array of highly interactive time series outputs, the dynamic relational configurations of which have substantial relevance when monitored over both brief and long time intervals and which can be used to generate improved alarm response.

Critical illness is one example of a complex dynamic timed process characterized by a plurality of interactive primary and compensatory outputs. When human physiologic stability is under threat, it is maintained by a complex array of interactive physiologic systems, which control the critical time dependent process of oxygen delivery to the organism. Each system (e.g. respiratory, cardiac or vascular) has multiple biochemical and/or mechanical controls, which operate together in a predictable manner to optimize oxygen delivery under conditions of threat. For example, a respiratory arrest (as with breath holding) causes a fall in heart rate to protect the heart muscle from the fall in oxygen. In addition to the basic control of a single system, other systems interact with the originally affected system to producing a predictable pattern of response.

Each system generally also has a plurality of predicable compensation responses to adjust for pathologic alteration or injury to the system and these responses interact between systems. For example the development of infectious injury to the lung will generally result in an increase in respiratory rate to compensate for the loss of functional surface area This increase in ventilation rate can then induce a synergistic increase in both stroke volume and heart rate.

Finally a pathologic process altering one system will generally also induce an alteration in one or more other systems and these processes are all time dependent. Sub acute or acute life threatening conditions such as sepsis, pulmonary embolism, or hemorrhage generally affect the systems in cascades or predictable sequences which may have a time course range from as little as 20 seconds or more than 72 hours. For example, the brief development of airway collapse induces a fall in oxygen saturation and a fall in heart rate. If the patient survives to arouse this causes a compensatory hyperventilation response, which causes a rise in heart rate and all of this may occur in over as little as 20-30 seconds alternately if they fail to arouse (as due to an adverse drug reaction) the respiratory arrest progressive fall in oxygen coupled with a fall in heart rate may progress to the state of dual arrest. The progression to this state may be greatly accelerated by the presence of poor ventricular function, electrical or conduction instability, or coronary disease. An infection, on the other hand, has a more prolonged time course often over a course of 48-72 hours—inducing a rise in respiration rate, a rise in heart rate, and then a progressive fall in oxygen saturation and finally respiratory arrest and a terminal fall in heart rate. As effective physiology compensation becomes exhausted, the final event of respiratory failure and arrest can occur precipitously during the night (when hospital staffing is low) thereby surprising the hospital staff with, what appears to be a sudden respiratory arrest.

As discussed in detail below, the present inventor recognized that precipitous pathophysiologic catastrophic events such as respiratory arrest are generally preceded by at least a brief episode of instability, which falls within a rage of definable patterns. He further recognized that both the instability and the catastrophic occurrence involves multiple interactive organ systems which produce definable relational patterns indicative of the occurrence which could then be exploited using a microprocessor to more timely recognize the adverse occurrence. Upon this realization he developed a system and method which provided signal integration and/or comparison of multiple signals, and in particular the patterns defined by multiple signals to define alarm threshold provided a better means to improve timely response to a catastrophic occurrences such as a respiratory arrest. According to the preset invention, the recognition of combined deviation of at least one parameter in combination with a fall in oxygen saturation (especially if the other parameter is identified and/or confirmed by another method such as EKG) can be used to generate an earlier alarm and a more reliable alarm.

As discussed in co pending application "Centralized hospital monitoring system for automatically detecting upper airway instability . . . ", filed May 17, 2002 (Which is incorporated by reference in its entirety, as if completely disclosed herein) and assigned to the present inventor, during health and disease, organs have a basal state (such a diastole, or functional residual capacity) and a variation (a reciprocation), away from, and back to, that basic state. At the organ level a physiologic control system, which can be anatomic, electrical, or chemical attempts to maintain normal ranges of the basal state and induces return toward the basal state. At higher levels a general basal state of the entire organism, and the interactive collective basal state of each organ, is generally maintained by a combination of interactive chemical, neural, and anatomic control. Upon variation from the basal state the physiologic control system will attempt to reverse the variation thereby producing reciprocation. The variation produces a compensatory response, which comprises a "companion reciprocation" which can be recognized by the processor and which improves the specificity of the recognition of the primary reciprocation. It can be seen that during very severe disease the attempt to achieve reversal may be unsuccessful so that reciprocations have the characteristic of being complete or incomplete. Interactive companion reciprocations operative from the cellular level to the organism level and exist across the entire range of time series scales and represent the fundamental link between the time series output of an organ or organism and the characterization of the operative control systems controlling that organ or organism, and the pathophysiologic process impacting the organ or organism.

As described in detail in provisional applications 60/291687 and 60/291691 (the contents of each of which are incorporated by reference as if completely disclosed herein), the present inventor recognized that the onset of the development of a catastrophic event represents the onset of a unique and critical relational time series of multiple signals (such as pulse rate, respiratory rate, and oxygen saturation) which is best considered as a relational process and tracked in close detail to generate a more specific output such as an alarm and so that the physician or nurse arriving to respond to the alarm can be immediately be provided with an interpreted output of the evolution of all of the monitored interactive parameters upon the onset of the occurrence which generated the alarm. The value of a monitoring device as a early warning system is therefore direct and close function of its ability to timely alarm in response to the actual onset of the occurrence of a precipitous life threatening event rather than the timeliness of its response to the occurrence of one or more threshold breaches along a single parameter (such as oxygen saturation). This is distinct from traditional thinking with respect to oximetry (see U.S. Pat. No. 5,865,763) where the focus has been to define the alarm either as a simple function of the occurrence of one or more crossings of a particular threshold value (such as an oxygen saturation below 85-90%) or as a function of the occurrence of a cumulative magnitude of values below a simple threshold. In fact the controversy within the standards committee of the FDA for oximetry alarm guidelines has been focused not defining the relationship of the alarm response to the relational outputs of a catastrophic occurrence, but rather upon defining which one-dimensional alarm warning threshold value of oxygen saturation should be uses (such as below 90% or below 85%). Such controversy misses the point, since, in the presence of precipitous catastrophic occurrence is not a given arbitrary threshold alarm value which is critical to functional survival but rather it is the value of time between the onset of the catastrophic event and the onset of the alarm which is best defined by the relational evolution of multiple parameters.

The present inventor recognized physicians, manufacturers, and hospitals have had a long unfulfilled need for an apparatus and method to alarm in response to the dynamic, real world pathophysiologic occurrences.

The present invention comprises a method and apparatus for providing an alarm based on a relational conformation of a plurality of time series and can include a pulse oximeter based microprocessor alarm system for the recognition of specific dynamic patterns of interaction between a plurality of corresponding and related time series, the system comprising a processor, the processor programmed to; process a first time series to produce to identify a first primary threshold breach based on said first time series, process at least a second time series, compare at least a portion of said first time series to at least said second time series to produce a comparison result, identify a relationship between said first time series and said second time series to identify a relational threshold breach, output an alarm based on at least one of said primary and said relational threshold breaches. The first time series is preferably oxygen saturation and the second time series can be pulse. Alternatively, the first time series can be the oxygen saturation of arterial blood and the second time series can be the respiration rate and or amplitude or a derivative of both the rate and amplitude (as by chest wall impedance). The relational breach can be a fall in oxygen saturation coupled with a fall in pulse. Another relational breach can be a fall in oxygen saturation coupled to a rise in respiration rate.

In one embodiment, the physician can select from a menu, which signals are to be included in the alarm response so that the alarm is tailored to the patient. According to the present invention, the system includes the conventional threshold based alarms to provide a floor of protection with the relational alarm system of the present invention included to provide more timely response upon the occurrence of instability or a precipitous life-threatening event such as respiratory arrest.

It is the purpose the present invention to provide a method and apparatus for providing dynamic alarm function of oximeters in response to precipitous catastrophic occurrences.

It is further the purpose of the present invention to provide a method and apparatus for promoting the sale of improved oximeters, which provide enhanced early warning characteristics, features, and functionality.

DESCRIPTION OF THE PRESENTLY PREFERRED EMBODIMENTS

Figure 1:
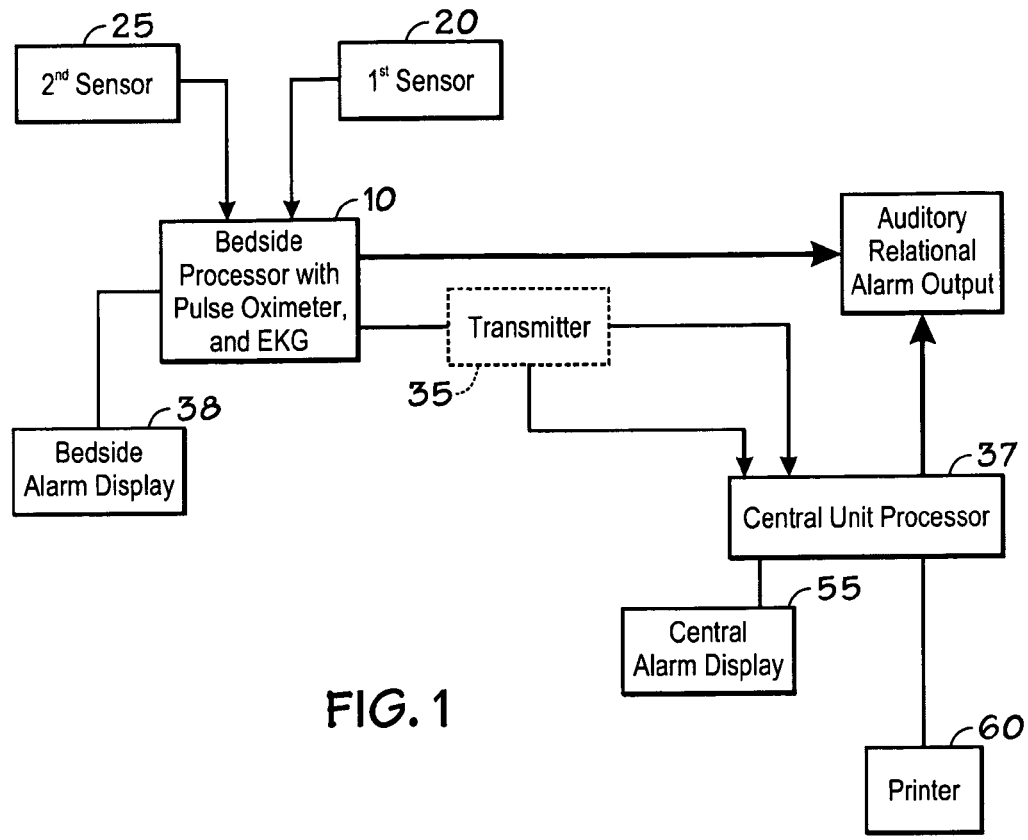
FIG. 1 shows a schematic of a relational alarm system according to the present invention.

FIG. 1 shows a relational alarm system for real time detection of a broad range of patterns and instabilities (as described in the aforementioned co pending patent application). The system includes a portable bedside monitor 10; which incorporates a pulse oximeter having at least a first sensor 20 and a electrocardiogram or other monitor including at least a second sensor 25. The system includes a transmitter 35 to a central processing unit 37. The bedside processor 10 preferably includes an output screen 38, which provides the nurse with a bedside indication of the sensor output. The central unit 37 preferably includes as output screen 55 and printer 60 for generating a hard copy for physician interpretation. According to present invention, and as discussed in detail in the aforementioned patent application, the system provides recognition and alarm of catastrophic occurrences based on analysis of relational outputs of a plurality of time series thereby allowing earlier and more specific recognition of respiratory arrest, airway instability, and complications related to such instability, and pathophysiologic divergence.

Figure 2:
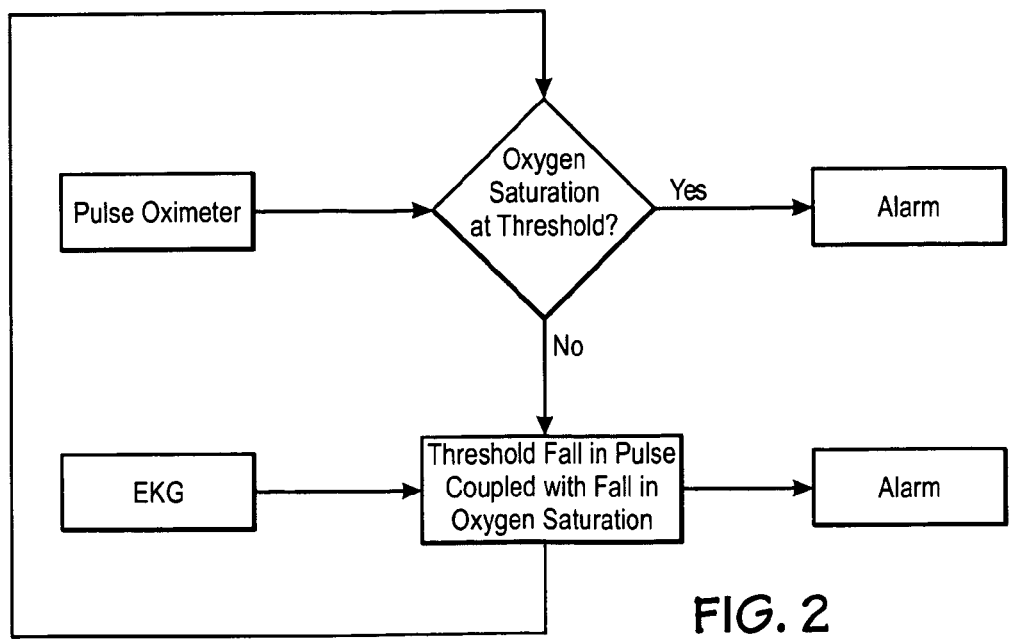
FIG. 2 shows a schematic of the processing method for analyzing a plurality of time series to provide earlier recognition of a pattern indicative of a particular a respiratory arrest according to the present invention and defining the time onset of an alarm of a pulse oximeter.

FIG. 2 shows a processing method for the relational alarm system. In one preferred embodiment the oxygen saturation is monitored along with the pulse rate (which is preferably derived from another sensor so that the same artifact is less likely to affect both sensors. In an example, as is conventional, if the processor identifies a fall in oxygen saturation or pulse that meets threshold (for example 85% and 50 respectively, the alarm sounds. However according to the present invention, if on the other hand the primary threshold is not reached but a secondary threshold is reached (for example a fall of 5% within 45 seconds) and there is a combined fall in oxygen saturation in association with a concurrent fall in heart rate (for example a fall of 8 or more beats per minute within 45 seconds) wherein the fall in heart rate developed in relation to the fall in oxygen saturation (immediately prior to, as for example 30 seconds or less), at the same time, or immediately thereafter) the alarm sounds indicating a relational output suggestive of an adverse event and that relational output is provided for over reading by the hospital worker. Here, it can be seen upon the teaching of the present invention that in the presence of adverse relational outputs, delaying the alarm until the primary 85% threshold breach is reached is not warranted or safe.

Upon this teaching those skilled in the art will recognize that many alternative relational outputs can be combined and analyzed along with oximetry (as by the time series analysis methods described in the aforementioned patent applications to the present inventor) to provide improved and more specific alarms and these are included within the scope of this teaching. For example a menu system for identifying the relational parameters to be including in the alarm could be provided. These can be selected by the user or coded in advance as set of alarm montages for application to a specific group of patients (e.g. based on the entered patient activity classification such as ambulatory, restless, quiet, comatose). The nurse could select specific relationships, which he or she desires for recognition and warning by the processor. According to the present invention the relational alarms could be customized to identify instability as well as a life-threatening occurrence. One example of instability warning would be an the selection of an alarm triggered by a relational pattern identified by the processor defined by a fall in oxygen saturation of X (say greater than or equal to 8%) coupled with a rise in respiration rate of Y (say 50% or more) lasting for at least Z (say 5-10 minutes). A relational pattern of signals falling within this range is highly indicative of respiratory instability. Accordingly, it is one of the express purposes of the present invention to provide for physicians and nurses, using these different warning relationships and patterns, considerably more functional and discretionary surveillance over different groups of patients.

Figure 3:
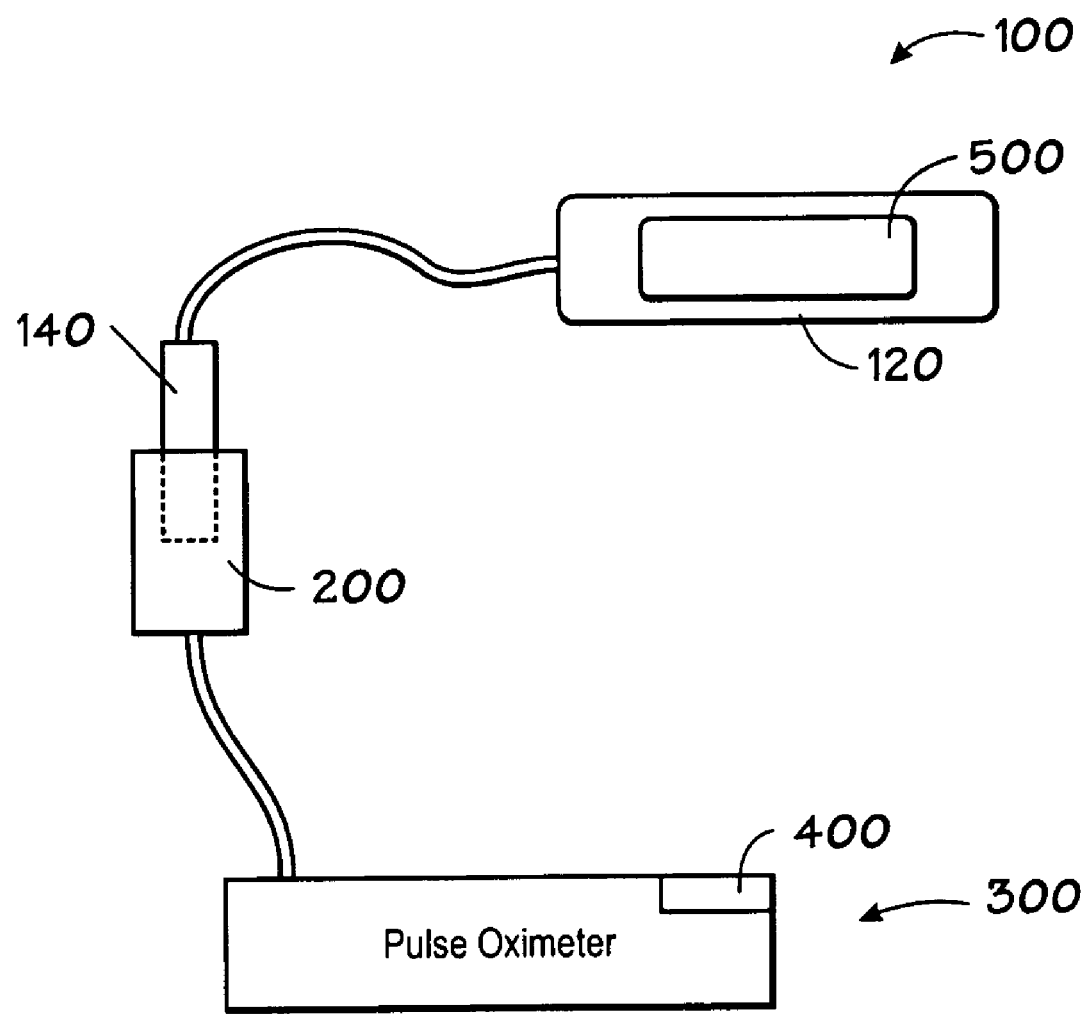
FIG. 3 shows a schematic of one preferred embodiment of the oximeter testing apparatus.
Figure 4:
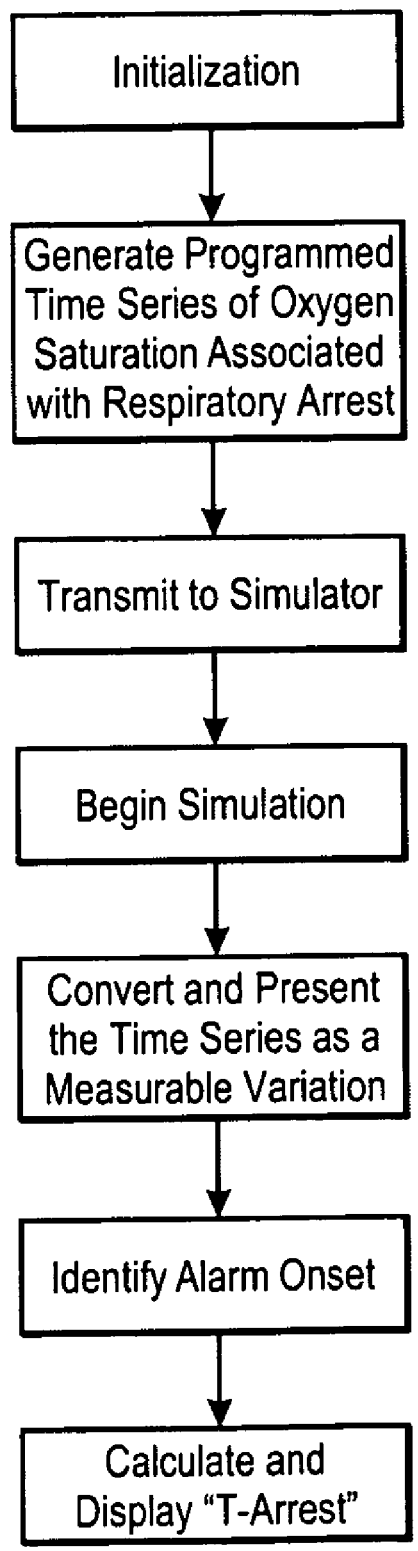
FIG. 4 shows one presently preferred processing method for testing of an oximetry systems ability to timely warn of a real world catastrophic occurrence using a respiratory arrest simulation

FIG. 3 shows one preferred embodiment of the oximeter testing apparatus 10, which can be used with a conventional oximeter or with a relational alarm based system of the present invention. The testing system includes a processor 12 in connection with a dynamic simulator 14 (which can be shaped to be received into a conventional finger probe) for interfacing with the probe 20 of an oximeter 30. A processor 12 controls the output of the simulator 14 according to the process of FIG. 4. The processor 12 is programmed to simulate the time series of arterial oxygen saturation and one or more additional parameters, which are generated in association with the occurrence of a precipitous apnea or respiratory arrest as from functional residual capacity. The programmed time series can be predicted by known formulas or, the time series of oxygen saturation and pulse (if also included) can be defined by or calculated from published clinical trials. In the preferred embodiment the simulated occurrence is a complete respiratory arrest occurring precipitously with the lung volume at functional residual capacity and at room air (21% oxygen) at the time of onset of the arrest. The dynamic oxygen saturation time series simulation for this occurrence can be, for example, the known delay and subsequent shape and slope of fall of the oxygen saturation time series (as can be calculated using known formulas for conversion of partial pressure of oxygen time series to oxygen saturation time series) as determined with breath holding clinical trials. (An example of such a clinical trial was published in Chest in 1996 entitled. "Arterial Blood Gas Changes during Breath-Holding from Functional Residual Capacity" by Sasse et. al.) The Severinghaus equation, or other formula, can be used to calculate the time series of oxygen saturations from the PaO2, PH, and PaCO2 values from clinical trials such as the one above which publish only the blood gas values. This can be coupled with the know range of falls in pulse if a relational monitor, according to the present invention is being tested.

The processor is programmed to output a baseline saturation (such as 97-100%) and then to begin (automatically or on command) the simulation of the precipitous respiratory arrest. The processor sets the clock at the onset of the simulated respiratory arrest. The processor is further programmed to then output a time series of oxygen saturation values with the predicted real time fall in oxygen saturation according to that predicted for such an event to the simulator for presentation to the probe. The time series of oxygen saturation values from the processor mirrors those calculated for the article noted or can be another time series, which mirrors the dynamic changes of oxygen saturation during a particular type of critical illness. In one preferred embodiment, an audio sensor is provided in connection with the processor, the sensor is responsive to the high frequency sound produced by the oximeter alarm. Upon the occurrence of the alarm, the sensor outputs an indication of the alarm occurrence to the processor, which records the time of onset of the alarm occurrence. Alternatively the time of onset of the alarm occurrence can be input by hand or automatically by connecting the processor of the oximeter and the processor of the testing device. The difference between the time of onset of the simulation of the respiratory arrest and onset of the alarm occurrence is calculated by the processor and outputted as the "TA" or "T-Arrest" value (given in seconds).

According to the present invention the "T-Arrest" is defined as: The time from the onset of a standardized respiratory arrest simulation to the onset of the alarm. This is a single number used to provide evidence of the performance of the oximeter as an early warning device. In one embodiment the T-Arrest is determined during motion and is given as the "TAM" or the "T-Arrest (Motion)". According to the present invention, oximeters will be marketed by publishing the TA and the TAM which (like the simple horsepower value in an automobile) will be used to determine performance. It is anticipated that, the present invention can be used by hospitals to test their existing oximeters and to test new devices before purchase. In the preferred embodiment the audio sensor has a threshold value equal to a decibel level, which is readily heard and recognized by a human ear.

If preferred the oximeter testing system can be incorporated into the oximeter as a self-testing method or process, which may, for example be initiated by keying in a "simulate physiology" button on the oximeter, which will then run an internal simulation and report the T-arrest. The menu could include a range of simulations, for example a time series with the alveolar oxygen at 21% at the onset of arrest in an adult, and then another with the alveolar oxygen at 40%, and a third which simulates a cardiac arrest with loss of the plethesmographic pulse, a fourth which simulates a respiratory arrest in a child or neonate. These internal simulations can be used for teaching purposes and can combine additional inputs such as pulse rate to test relational alarm features if provided. In an alternative embodiment the menu can include the selection of the inspired oxygen level and the occurrence of a specific level of ventilation (minute ventilation) and dead space.

Alternative configurations of the simulator can included include the addition of a transmitter for transmitting the simulated oxygen saturation output from the processor to a receiver of a separate simulator for interfacing with the probe of an oximeter at a remote location such as a patient's room. Hospitals can position a given oximeter at a bedside and the alarm testing device at the nurses station and then initiate the testing sequence to determine if the alarm will be recognized by the nurses at the station and how long after an arrest they will hear the alarm with a given oximeter (if at all). The processor can include an audio sensor 40 capable of providing an output indicative of the occurrence of an audio alarm at a specified decibel level. The processor can also include an input indicator for manually indicating when action has been taken (e.g. the time at which the beside has been reached with the ventilation equipment in hand.)

In operation the probe 200 is connected to the simulator 140 of the alarm testing system 100, as in a patients room. The operator then inputs to initiate the simulation. The simulation is then initiated. The processor transmits the simulated saturation time series based on the time series predicted form the occurrence of a respiratory arrest to the simulator 140 as previously discussed and records the time of onset of the simulation. The simulator 140 presents to the probe 200 a measurable timed variation indicative of the saturation time series. When the oximeter 300 generates an auditory alarm at the specified decibel level in response to the outputs of the simulator 140, to the site of the processor 120, the time of onset of the alarm is recorded and the difference between the time of onset of the arrest simulation and the time of onset of the alarm is calculated and presented on the display 500. In some situations the oximeter under test may also include a transmitter, which transmits the oxygen saturation output back to a central nursing station where the alarm will sound. Since such transmissions also may include averaging intervals or long intervals (20 seconds) between sample transmissions, the effect of this delay can also be determined by this system 100. The system 100 can be used for spot (surprise) checks of the alarm response times in a nursing ward where all of the factors; patient physiologic delay, signal processing delay, transmission delay, alarm output delay, personnel response delay, and the delay associated with the time to reach the bedside (where the nurse inputs the endpoint), are automatically included providing a true index of the effective hospital response to an actual alarm indicative of a life threatening event.

It will be evident to those skilled in the art that many additional modifications may be made, and these are included within the scope of the invention.

What is claimed is:

1. A method of processing data comprising a plurality of related time series, comprising:
    searching a first one of the plurality of time series for data corresponding to a primary threshold breach;
    producing an alarm output if data corresponding to the primary threshold breach is discovered;
    searching the first one of the plurality of time series and a second one of the plurality of time series for data corresponding to a relationship between the first one of the plurality of time series and the second one of the plurality of time series;
    searching data corresponding to the relationship for data corresponding to a relational threshold breach; and
    producing an output indicative of the relational threshold breach if data corresponding to the relational threshold breach is discovered,
    wherein the second one of the plurality of time series corresponds to timed ventilation.

2. The method of claim 1, wherein the output indicative of the relational threshold breach comprises an alarm.

3. The method of claim 1, wherein the first one of the plurality of time series comprises data corresponding to a physiologic parameter of a patient.

4. The method of claim 1, wherein the first one of the plurality of time series corresponds to oxygen saturation.

5. The method of claim 1, wherein the relationship comprises at least one pattern relationship.

6. The method of claim 5, wherein the pattern relationship comprises downward sloping oxygen saturation.

7. The method of claim 1, wherein the relationship comprises at least one trending relationship.

8. A method of processing data comprising a plurality of related time series, comprising:
    searching a first one of the plurality of time series for data corresponding to a primary threshold breach;
    producing an alarm output if data corresponding to the primary threshold breach is discovered;
    searching the first one of the plurality of time series and a second one of the plurality of time series for data corresponding to a relationship between the first one of the plurality of time series and the second one of the plurality of time series;
    searching data corresponding to the relationship for data corresponding to a relational threshold breach; and
    producing an output indicative of the relational threshold breach if data corresponding to the relational threshold breach is discovered,
    wherein the second one of the plurality of time series corresponds to a respiratory rate.

9. A method of processing data comprising a plurality of related time series, comprising:
    searching a first one of the plurality of time series for data corresponding to a primary threshold breach;

producing an alarm output if data corresponding to the primary threshold breach is discovered;
searching the first one of the plurality of time series and a second one of the plurality of time series for data corresponding to a relationship between the first one of the plurality of time series and the second one of the plurality of time series;
searching data corresponding to the relationship for data corresponding to a relational threshold breach; and
producing an output indicative of the relational threshold breach if data corresponding to the relational threshold breach is discovered,
wherein the second one of the plurality of time series corresponds to a respiratory amplitude.

10. A method of processing data comprising a plurality of related time series, comprising:
searching a first one of the plurality of time series for data corresponding to a primary threshold breach;
producing an alarm output if data corresponding to the primary threshold breach is discovered;
searching the first one of the plurality of time series and a second one of the plurality of time series for data corresponding to a relationship between the first one of the plurality of time series and the second one of the plurality of time series;
searching data corresponding to the relationship for data corresponding to a relational threshold breach; and
producing an output indicative of the relational threshold breach if data corresponding to the relational threshold breach is discovered,
wherein the second one of the plurality of time series corresponds to a derivative of both a respiratory rate and a respiratory amplitude.

11. A method of processing data comprising a plurality of related time series, comprising:
searching a first one of the plurality of time series for data corresponding to a primary threshold breach;
producing an alarm output if data corresponding to the primary threshold breach is discovered;
searching the first one of the plurality of time series and a second one of the plurality of time series for data corresponding to a relationship between the first one of the plurality of time series and the second one of the plurality of time series;
searching data corresponding to the relationship for data corresponding to a relational threshold breach; and
producing an output indicative of the relational threshold breach if data corresponding to the relational threshold breach is discovered,
wherein the second one of the plurality of time series corresponds to a magnitude of timed ventilation.

12. A method of processing data comprising a plurality of related time series, comprising:
searching a first one of the plurality of time series for data corresponding to a primary threshold breach;
producing an alarm output if data corresponding to the primary threshold breach is discovered;
searching the first one of the plurality of time series and a second one of the plurality of time series for data corresponding to a relationship between the first one of the plurality of time series and the second one of the plurality of time series;
searching data corresponding to the relationship for data corresponding to a relational threshold breach; and
producing an output indicative of the relational threshold breach if data corresponding to the relational threshold breach is discovered,
wherein the relationship comprises a fall in oxygen saturation coupled to a rise in respiration rate.

13. A method of processing data comprising a plurality of related time series, comprising:
searching a first one of the plurality of time series for data corresponding to a primary threshold breach;
producing an alarm output if data corresponding to the primary threshold breach is discovered;
searching the first one of the plurality of time series and a second one of the plurality of time series for data corresponding to a relationship between the first one of the plurality of time series and the second one of the plurality of time series;
searching data corresponding to the relationship for data corresponding to a relational threshold breach; and
producing an output indicative of the relational threshold breach if data corresponding to the relational threshold breach is discovered,
wherein the relationship is a derivative of both a parameter rate and a parameter amplitude.

14. A method of processing data comprising a plurality of related time series, comprising:
searching a first one of the plurality of time series for data corresponding to a primary threshold breach;
searching the first one of the plurality of time series and a second one of the plurality of time series for data corresponding to a relationship between the first one of the plurality of time series and the second one of the plurality of time series, the relationship being independent of the primary threshold breach;
searching data corresponding to the relationship for data corresponding to a relational threshold breach; and
producing an output indicative of at least one of the primary threshold breach and the relational threshold breach if data corresponding to such a breach is discovered, wherein the relationship comprises an indication of ventilation by chest wall impedance.

15. A method of processing data comprising a plurality of related time series, comprising:
searching a first one of the plurality of time series for data corresponding to a primary threshold breach;
searching the first one of the plurality of time series and a second one of the plurality of time series for data corresponding to a relationship between the first one of the plurality of time series and the second one of the plurality of time series, the relationship being independent of the primary threshold breach;
searching data corresponding to the relationship for data corresponding to a relational threshold breach; and
producing an output indicative of at least one of the primary threshold breach and the relational threshold breach if data corresponding to such a breach is discovered, wherein the second one of the plurality of time series corresponds to timed ventilation.

16. The method of claim 15, wherein the output comprises an alarm.

17. The method of claim 15, wherein the first one of the plurality of time series comprises data corresponding to a physiologic parameter of a patient.

18. The method of claim 15, wherein the first one of the plurality of time series corresponds to oxygen saturation.

19. The method of claim 15, wherein the relationship comprises at least one pattern relationship.

20. The method of claim 19, wherein the pattern relationship comprises downward sloping oxygen saturation.

21. The method of claim 15, wherein the relationship comprises at least one trending relationship.

22. A method of processing data comprising a plurality of related time series, comprising:
    searching a first one of the plurality of time series for data corresponding to a primary threshold breach;
    searching the first one of the plurality of time series and a second one of the plurality of time series for data corresponding to a relationship between the first one of the plurality of time series and the second one of the plurality of time series, the relationship being independent of the primary threshold breach;
    searching data corresponding to the relationship for data corresponding to a relational threshold breach; and
    producing an output indicative of at least one of the primary threshold breach and the relational threshold breach if data corresponding to such a breach is discovered, wherein the second one of the plurality of time series corresponds to a respiratory rate.

23. A method of processing data comprising a plurality of related time series, comprising:
    searching a first one of the plurality of time series for data corresponding to a primary threshold breach;
    searching the first one of the plurality of time series and a second one of the plurality of time series for data corresponding to a relationship between the first one of the plurality of time series and the second one of the plurality of time series, the relationship being independent of the primary threshold breach;
    searching data corresponding to the relationship for data corresponding to a relational threshold breach; and
    producing an output indicative of at least one of the primary threshold breach and the relational threshold breach if data corresponding to such a breach is discovered, wherein the second one of the plurality of time series corresponds to a respiratory amplitude.

24. A method of processing data comprising a plurality of related time series, comprising:
    searching a first one of the plurality of time series for data corresponding to a primary threshold breach;
    searching the first one of the plurality of time series and a second one of the plurality of time series for data corresponding to a relationship between the first one of the plurality of time series and the second one of the plurality of time series, the relationship being independent of the primary threshold breach;
    searching data corresponding to the relationship for data corresponding to a relational threshold breach; and
    producing an output indicative of at least one of the primary threshold breach and the relational threshold breach if data corresponding to such a breach is discovered, wherein the second one of the plurality of time series corresponds to a derivative of both a respiratory rate and a respiratory amplitude.

25. A method of processing data comprising a plurality of related time series, comprising:
    searching a first one of the plurality of time series for data corresponding to a primary threshold breach;
    searching the first one of the plurality of time series and a second one of the plurality of time series for data corresponding to a relationship between the first one of the plurality of time series and the second one of the plurality of time series, the relationship being independent of the primary threshold breach;
    searching data corresponding to the relationship for data corresponding to a relational threshold breach; and
    producing an output indicative of at least one of the primary threshold breach and the relational threshold breach if data corresponding to such a breach is discovered, wherein the second one of the plurality of time series corresponds to a magnitude of timed ventilation.

26. A method of processing data comprising a plurality of related time series, comprising:
    searching a first one of the plurality of time series for data corresponding to a primary threshold breach;
    searching the first one of the plurality of time series and a second one of the plurality of time series for data corresponding to a relationship between the first one of the plurality of time series and the second one of the plurality of time series, the relationship being independent of the primary threshold breach;
    searching data corresponding to the relationship for data corresponding to a relational threshold breach; and
    producing an output indicative of at least one of the primary threshold breach and the relational threshold breach if data corresponding to such a breach is discovered, wherein the relationship comprises a fall in oxygen saturation coupled to a rise in respiration rate.

27. A method of processing data comprising a plurality of related time series, comprising:
    searching a first one of the plurality of time series for data corresponding to a primary threshold breach;
    searching the first one of the plurality of time series and a second one of the plurality of time series for data corresponding to a relationship between the first one of the plurality of time series and the second one of the plurality of time series, the relationship being independent of the primary threshold breach;
    searching data corresponding to the relationship for data corresponding to a relational threshold breach; and
    producing an output indicative of at least one of the primary threshold breach and the relational threshold breach if data corresponding to such a breach is discovered, wherein the relationship is a derivative of both a parameter rate and a parameter amplitude.

28. A method of processing data comprising a plurality of related time series, comprising:
    searching a first one of the plurality of time series for data corresponding to a primary threshold breach;
    searching the first one of the plurality of time series and a second one of the plurality of time series for data corresponding to a relationship between the first one of the plurality of time series and the second one of the plurality of time series, the relationship being independent of the primary threshold breach;
    searching data corresponding to the relationship for data corresponding to a relational threshold breach; and
    producing an output indicative of at least one of the primary threshold breach and the relational threshold breach if data corresponding to such a breach is discovered, wherein the relationship comprises an indication of ventilation by chest wall impedance.

29. A method of processing data comprising a plurality of related time series, comprising:
    searching a first one of the plurality of time series and a second one of the plurality of time series for data corresponding to a first relationship between the first one of the plurality of time series and the second one of the plurality of time series;
    identifying a first relational threshold breach if data corresponding to the first relationship exceeds a first threshold value;
    searching the first one of the plurality of time series and the second one of the plurality of time series for data corresponding to a second relationship between the first one of the plurality of time series and the second one of the plurality of time series, the second relationship being different than the first relationship;

identifying a second relational threshold breach if data corresponding to the second relationship exceeds a second threshold value; and producing an output indicative of at least one of the first relational threshold breach and the second relational threshold breach.

30. The method of claim 29, wherein the output comprises an alarm.

31. The method of claim 29, wherein the first one of the plurality of time series comprises data corresponding to a physiologic parameter of a patient.

32. The method of claim 29, wherein the second one of the plurality of time series comprises data corresponding to a physiologic parameter of a patient.

33. The method of claim 29, wherein the first one of the plurality of time series corresponds to oxygen saturation.

34. The method of claim 29, wherein the second one of the plurality of time series corresponds to timed ventilation.

35. The method of claim 29, wherein the second one of the plurality of time series corresponds to a respiratory rate.

36. The method of claim 29, wherein the second one of the plurality of time series corresponds to a respiratory amplitude.

37. The method of claim 29, wherein the second one of the plurality of time series corresponds to a derivative of both a respiratory rate and a respiratory amplitude.

38. The method of claim 29, wherein the second one of the plurality of time series corresponds to a magnitude of timed ventilation.

39. The method of claim 29, wherein the first relationship comprises at least one pattern relationship.

40. The method of claim 39, wherein the pattern relationship comprises downward sloping oxygen saturation.

41. The method of claim 29, wherein the first relationship comprises at least one trending relationship.

42. The method of claim 29, wherein the first relationship comprises a fall in oxygen saturation coupled to a rise in respiration rate.

43. The method of claim 29, wherein the first relationship is a derivative of both a parameter rate and a parameter amplitude.

44. The method of claim 29, wherein the first relationship comprises an indication of ventilation by chest wall impedance.

* * * * *